(12) United States Patent
Jahrmarkt

(10) Patent No.: US 9,943,668 B2
(45) Date of Patent: Apr. 17, 2018

(54) GUIDEWIRE AND CATHETER SYSTEM AND METHOD FOR TREATING A BLOOD CLOT

(71) Applicant: Sub3 Vascular, LLC, Miami Beach, FL (US)

(72) Inventor: Scott L. Jahrmarkt, Miami Beach, FL (US)

(73) Assignee: SUB3 VASCULAR, LLC, Miami Beach, FL (US)

( * ) Notice: Subject to any disclaimer, the term of this patent is extended or adjusted under 35 U.S.C. 154(b) by 559 days.

(21) Appl. No.: 14/524,982

(22) Filed: Oct. 27, 2014

(65) Prior Publication Data

US 2016/0114138 A1    Apr. 28, 2016

(51) Int. Cl.
*A61M 25/09*    (2006.01)
*A61M 1/00*    (2006.01)
(Continued)

(52) U.S. Cl.
CPC ............ *A61M 25/09* (2013.01); *A61M 1/008* (2013.01); *A61M 25/1025* (2013.01);
(Continued)

(58) Field of Classification Search
CPC .................. A61M 25/09; A61M 1/008; A61M 25/10184; A61M 25/1025;
(Continued)

(56) References Cited

U.S. PATENT DOCUMENTS 5,002,560 A    3/1991    Machold et al.
5,087,244 A    2/1992    Wolinsky et al.
(Continued)

FOREIGN PATENT DOCUMENTS

EP    0277366    8/1988
EP    0380227    8/1990
(Continued)

OTHER PUBLICATIONS

"Intravascular Ultrasound Assessment of the Novel AngioSculpt® Scoring Balloon Catheter for the Treatment of Complex Coronary L", Alberto Fonseca, MD et al., The Journal of Invasive Cardiology, vol. 20, Issue No. 1, Publication Date: Jan. 24, 2008; available at http://www.invasivecardiology.com/article/8260.

*Primary Examiner* — Bhisma Mehta
*Assistant Examiner* — Hamza Darb
(74) *Attorney, Agent, or Firm* — Gordon & Jacobson, P.C.

(57) ABSTRACT

A system for treating vasculature of a patient includes a microcatheter extending through an optional aspiration catheter, and a guidewire subassembly extending through and beyond the microcatheter. The guidewire subassembly consists essentially of a (i) guidewire core having a narrowed portion, (ii) a fluid transport element coupled to and extending around the narrowed portion of the guidewire core, the fluid transport element defining at least one inlet opening and at least one outlet opening spaced from the inlet opening along a portion of its length, with a fluid flow path being defined between the fluid transport element and the microcatheter, and (iii) a conical seal interposed between the guidewire core and the support element for sealing therebetween and ensuring that infusate within the microcatheter is directed into the blood vessel through the inlet opening(s), the fluid flow path, and the outlet opening(s).

15 Claims, 16 Drawing Sheets

(51) Int. Cl.
*A61M 25/10* (2013.01)
*A61M 25/00* (2006.01)

(52) U.S. Cl.
CPC .............. *A61M 25/10184* (2013.11); *A61M 2025/0042* (2013.01); *A61M 2025/091* (2013.01); *A61M 2025/09008* (2013.01); *A61M 2025/09133* (2013.01); *A61M 2025/09175* (2013.01); *A61M 2210/0693* (2013.01)

(58) Field of Classification Search
CPC ........... A61M 2210/0693; A61M 2025/09008; A61M 2025/091; A61M 2025/09175; A61M 2025/0042
See application file for complete search history.

(56) References Cited

U.S. PATENT DOCUMENTS

| | | |
|---|---|---|
| 5,100,423 A | 3/1992 | Fearnot |
| 5,295,962 A | 3/1994 | Crocker et al. |
| 5,421,826 A | 6/1995 | Crocker et al. |
| 5,449,343 A * | 9/1995 | Samson ............ A61M 25/0138 604/103.1 |
| 5,490,859 A | 2/1996 | Miche et al. |
| 5,501,694 A | 3/1996 | Ressemann et al. |
| 5,540,707 A | 7/1996 | Ressemann et al. |
| 5,542,926 A | 8/1996 | Crocker |
| 5,558,643 A | 9/1996 | Samson et al. |
| 5,569,184 A | 10/1996 | Crocker et al. |
| 5,569,197 A | 10/1996 | Helmus et al. |
| 5,584,803 A | 12/1996 | Stevens et al. |
| 5,702,368 A | 12/1997 | Stevens et al. |
| 5,730,734 A | 3/1998 | Adams et al. |
| 5,769,812 A | 6/1998 | Stevens et al. |
| 5,769,821 A | 6/1998 | Abrahamson et al. |
| 5,792,094 A | 8/1998 | Stevens et al. |
| 5,792,157 A | 8/1998 | Mische et al. |
| 5,795,331 A | 8/1998 | Cragg et al. |
| 5,836,868 A | 11/1998 | Ressemann et al. |
| 5,843,050 A * | 12/1998 | Jones ................ A61M 25/0012 604/525 |
| 5,868,702 A | 2/1999 | Stevens et al. |
| 5,868,719 A | 2/1999 | Tsukernik |
| 5,885,238 A | 3/1999 | Stevens et al. |
| 5,897,567 A | 4/1999 | Ressemann et al. |
| 5,904,698 A | 5/1999 | Thomas et al. |
| 5,908,405 A | 6/1999 | Imran et al. |
| 5,935,145 A | 8/1999 | Villar et al. |
| 5,941,871 A | 8/1999 | Adams et al. |
| 5,972,019 A | 10/1999 | Engelson et al. |
| 5,989,208 A | 11/1999 | Nita |
| 5,993,374 A | 11/1999 | Kick |
| 6,011,995 A | 1/2000 | Guglielmi et al. |
| 6,053,911 A | 4/2000 | Ryan et al. |
| 6,146,396 A | 11/2000 | Konya et al. |
| 6,234,996 B1 | 5/2001 | Bagaoisan et al. |
| 6,254,588 B1 | 7/2001 | Jones et al. |
| 6,306,124 B1 | 10/2001 | Jones et al. |
| 6,454,741 B1 | 9/2002 | Muni et al. |
| 6,500,147 B2 * | 12/2002 | Omaleki ............... A61M 25/09 604/103.09 |
| 6,506,194 B1 | 1/2003 | Hajianpour |
| 6,506,202 B1 | 1/2003 | Dutta et al. |
| 6,565,555 B1 | 5/2003 | Ryan et al. |
| 6,569,148 B2 | 5/2003 | Bagaoisan et al. |
| 6,648,854 B1 | 11/2003 | Patterson et al. |
| 6,652,480 B1 | 11/2003 | Imran et al. |
| 6,652,548 B2 | 11/2003 | Evans et al. |
| 6,669,670 B1 | 12/2003 | Muni et al. |
| 6,685,718 B1 | 2/2004 | Wyzgala et al. |
| 6,685,722 B1 | 2/2004 | Rosenbluth et al. |
| 6,709,427 B1 | 3/2004 | Nash et al. |
| 6,726,651 B1 | 4/2004 | Robinson et al. |
| 6,770,070 B1 | 8/2004 | Balbierz |
| 6,802,825 B2 | 10/2004 | Ackerman et al. |
| 6,824,550 B1 | 11/2004 | Noriega et al. |
| 6,855,136 B2 | 2/2005 | Dorros et al. |
| 6,866,650 B2 | 3/2005 | Stevens et al. |
| 6,890,339 B2 | 5/2005 | Sahatjian et al. |
| 6,899,716 B2 | 5/2005 | Cragg |
| 6,921,403 B2 | 7/2005 | Cragg et al. |
| 6,942,613 B2 | 9/2005 | Ewers et al. |
| 6,955,661 B1 | 10/2005 | Herweck et al. |
| 6,960,162 B2 | 11/2005 | Saadat et al. |
| 6,960,163 B2 | 11/2005 | Ewers et al. |
| 6,994,689 B1 | 2/2006 | Zadno-Azizi et al. |
| 7,033,344 B2 | 4/2006 | Imran |
| 7,108,704 B2 | 9/2006 | Trerotola |
| 7,150,737 B2 | 12/2006 | Purdy et al. |
| RE39,668 E | 5/2007 | Bagaoisan et al. |
| 7,252,674 B2 | 8/2007 | Wyzgala et al. |
| 7,278,991 B2 | 10/2007 | Morris et al. |
| 7,309,334 B2 | 12/2007 | von Hoffmann |
| 7,322,958 B2 | 1/2008 | Wholey et al. |
| 7,329,259 B2 | 2/2008 | Cragg |
| 7,374,560 B2 | 5/2008 | Ressemann et al. |
| 7,419,482 B2 | 9/2008 | Nash et al. |
| 7,422,586 B2 | 9/2008 | Morris et al. |
| 7,442,192 B2 | 10/2008 | Knowlton |
| 7,465,286 B2 | 12/2008 | Patterson et al. |
| 7,517,352 B2 | 4/2009 | Evans et al. |
| 7,594,900 B1 | 9/2009 | Nash et al. |
| 7,604,612 B2 | 10/2009 | Ressemann et al. |
| 7,608,077 B2 | 10/2009 | Cragg et al. |
| 7,625,371 B2 | 12/2009 | Morris et al. |
| 7,628,763 B2 | 12/2009 | Noriega et al. |
| 2002/0002383 A1 | 1/2002 | Sepetka et al. |
| 2002/0143361 A1 | 10/2002 | Douk et al. |
| 2009/0287166 A1 | 11/2009 | Dang |

FOREIGN PATENT DOCUMENTS

| | | |
|---|---|---|
| WO | WO 92/11896 | 7/1992 |
| WO | WO 92/13566 | 8/1992 |
| WO | WO 92/15282 | 9/1992 |
| WO | WO 93/11751 | 6/1993 |
| WO | WO 03/018085 | 3/2003 |
| WO | WO 03/043533 | 5/2003 |
| WO | WO 2004/062513 | 7/2004 |
| WO | WO 2006/031410 | 3/2006 |
| WO | WO 2008/063621 | 5/2008 |
| WO | WO 2012/009518 | 1/2012 |
| WO | WO 2012009518 A1 * | 1/2012 ............ A61M 25/09 |

* cited by examiner

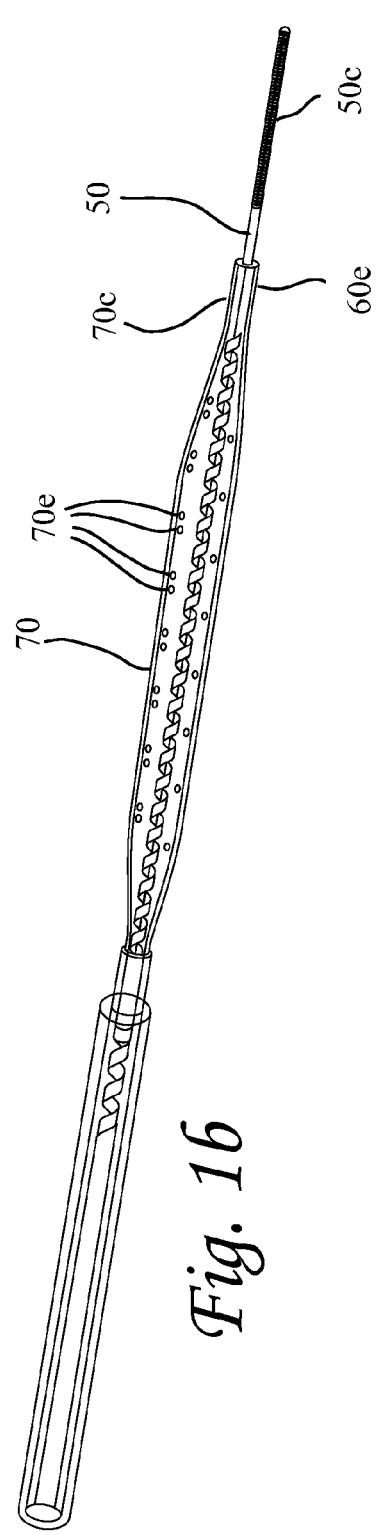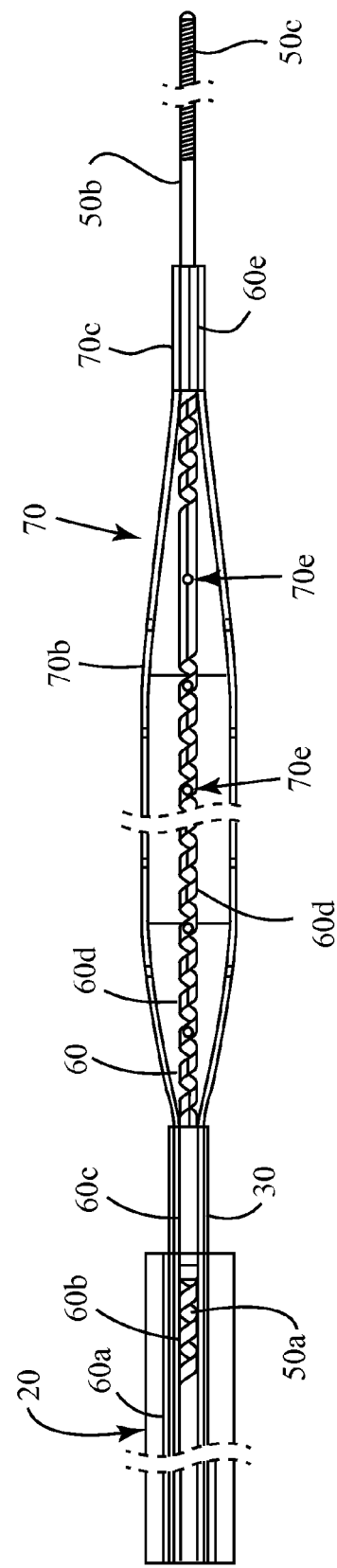

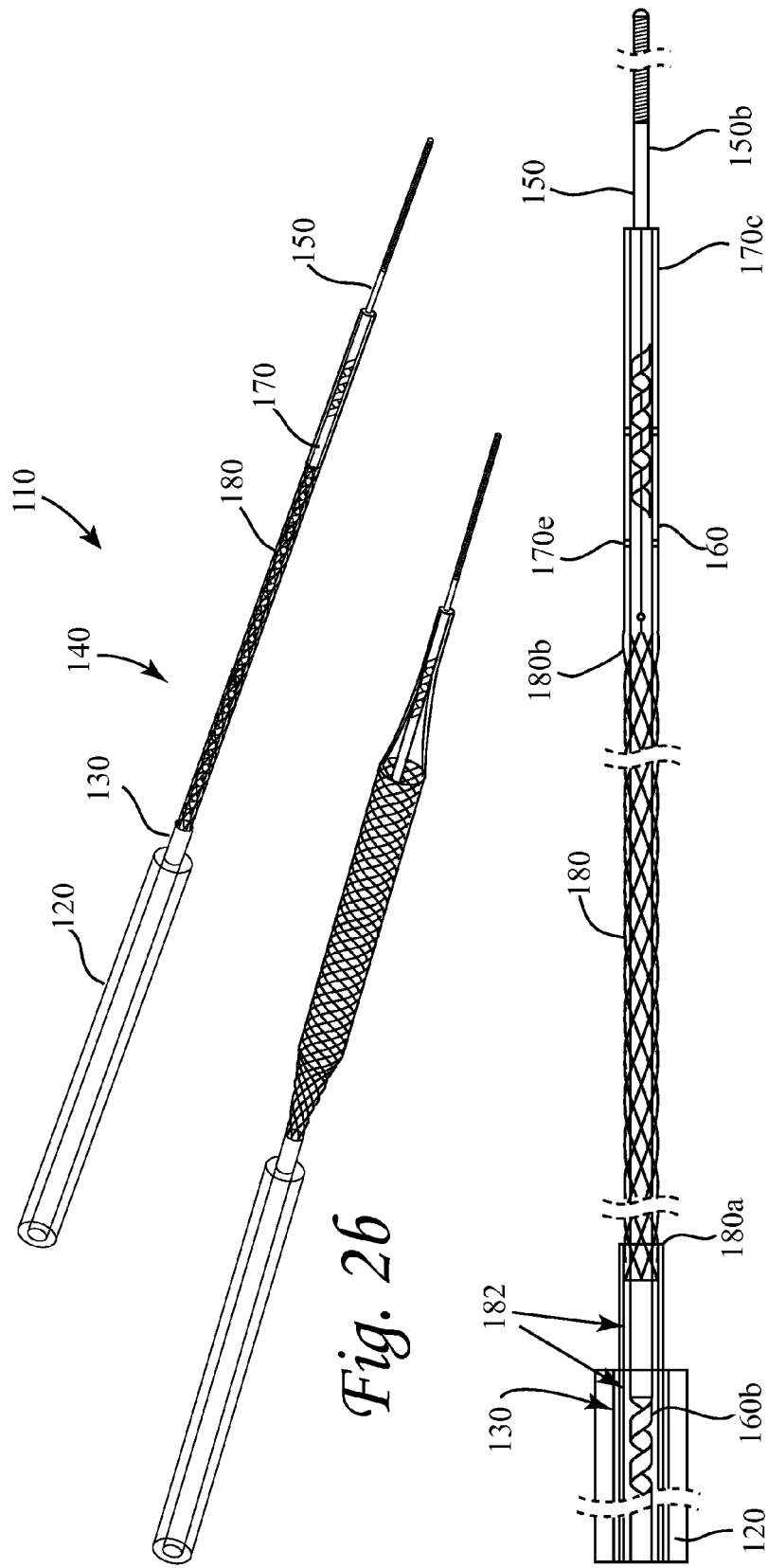

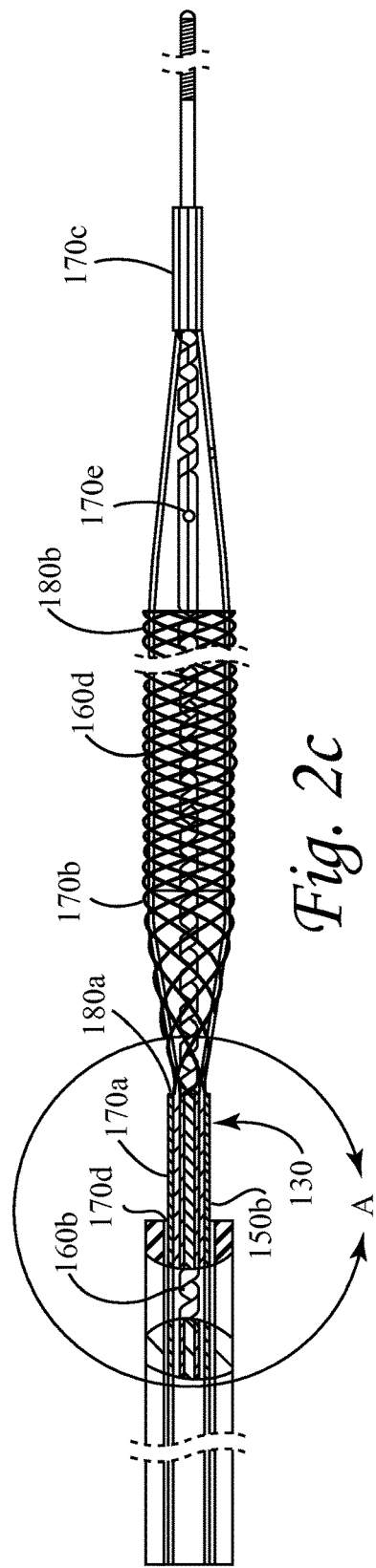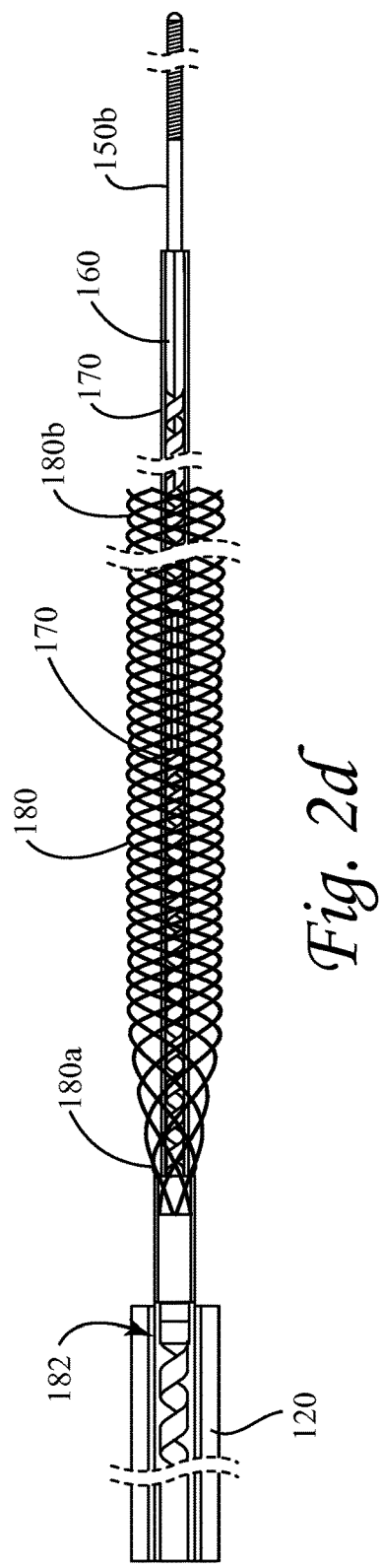

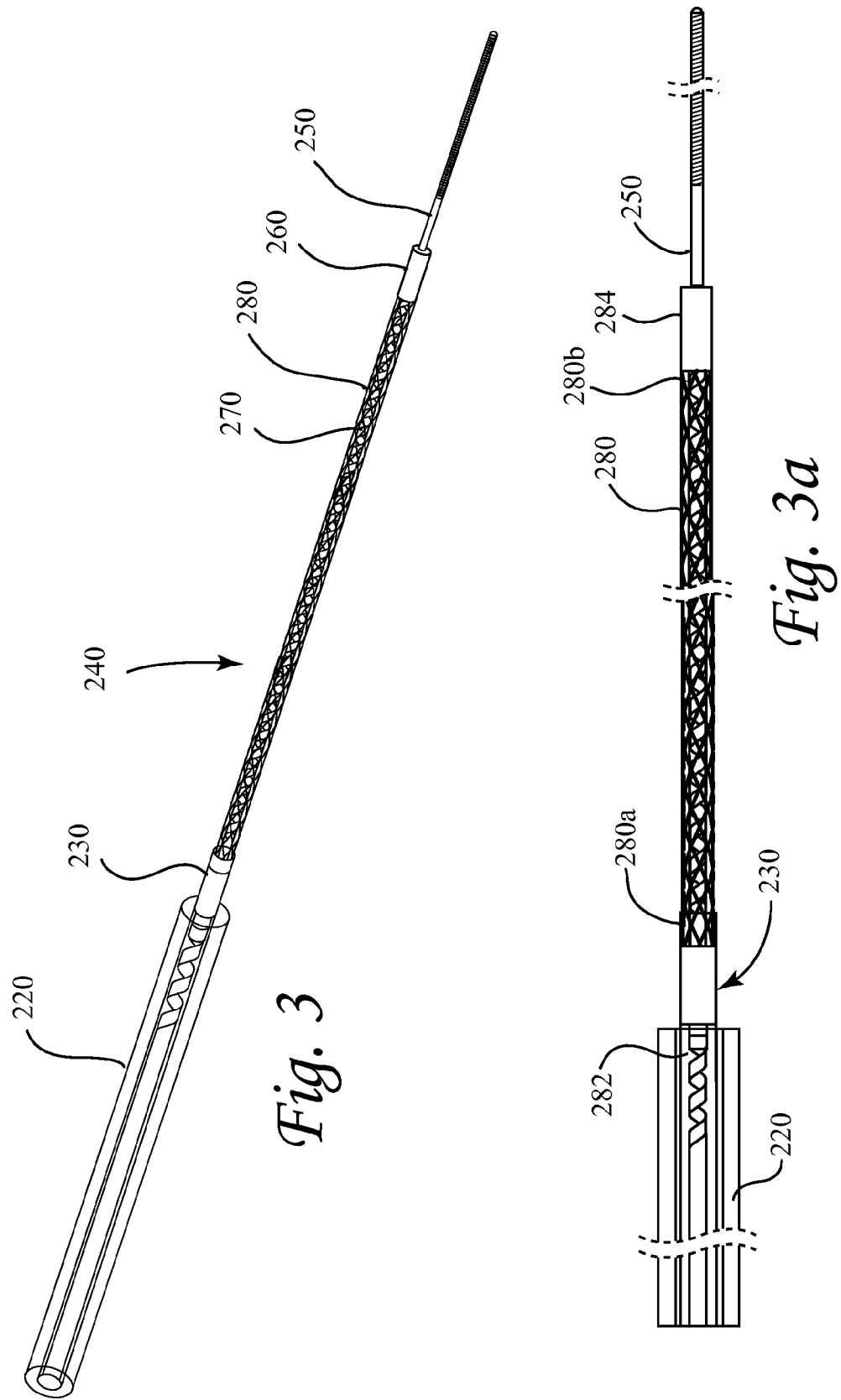

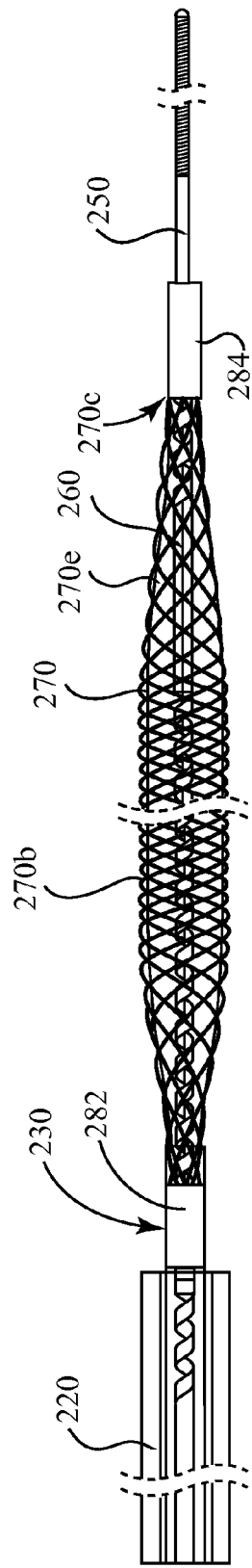
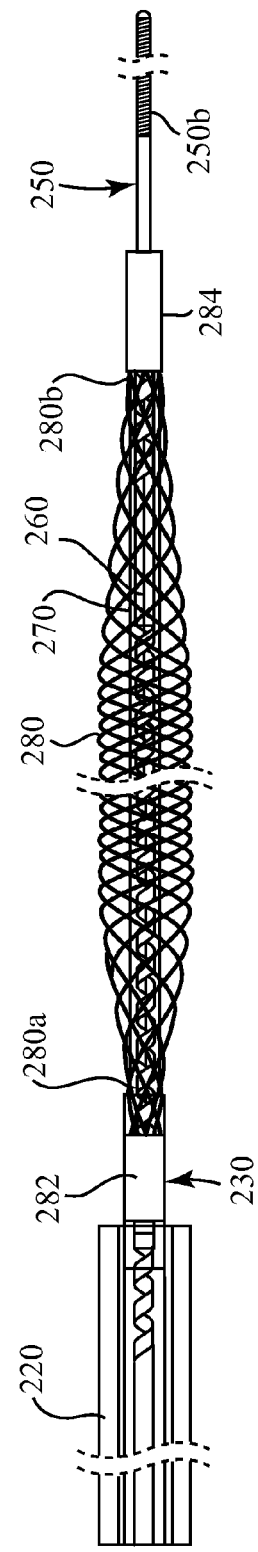

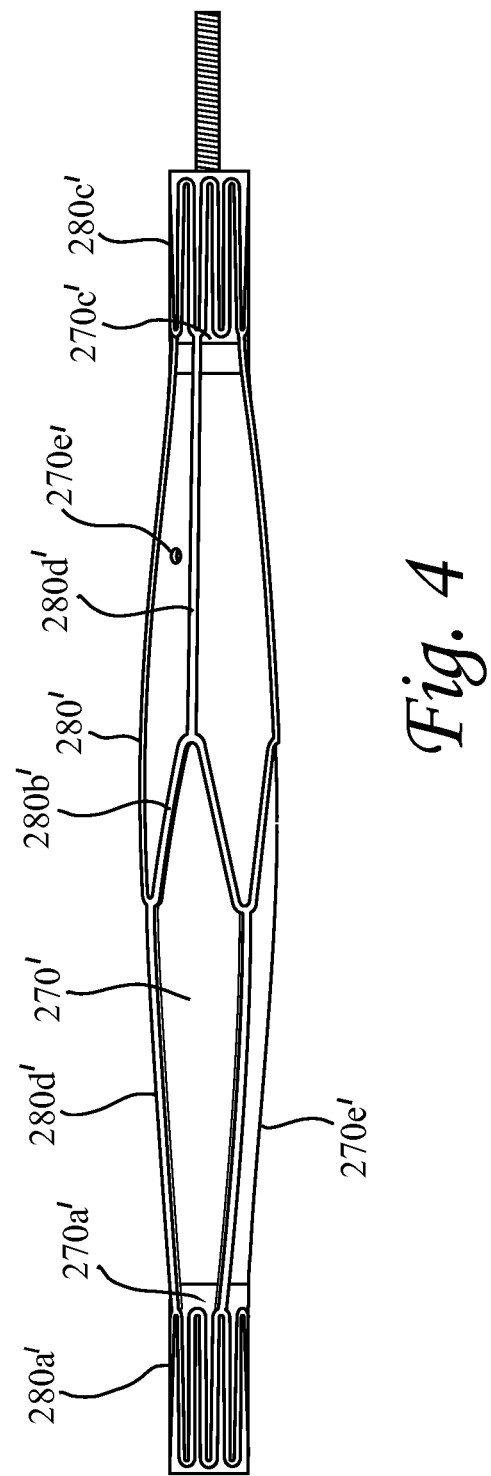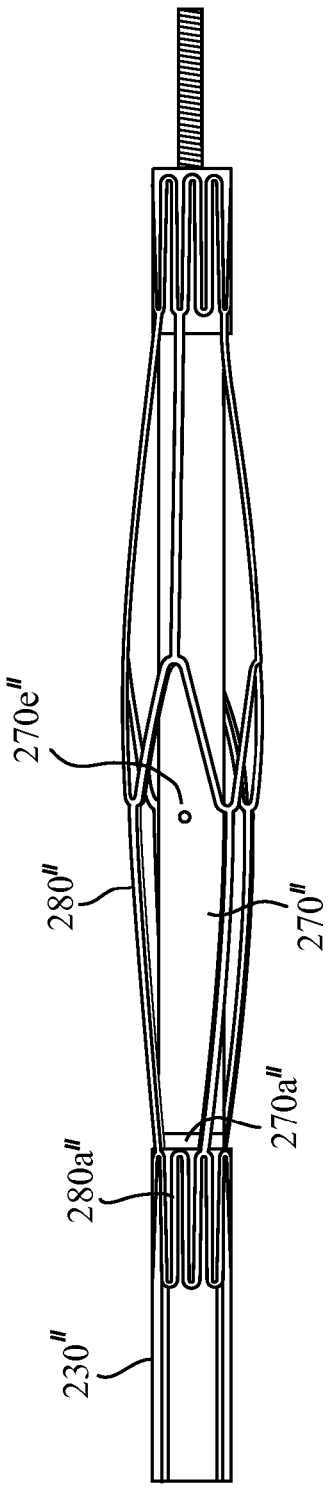
Fig. 4
Fig. 5

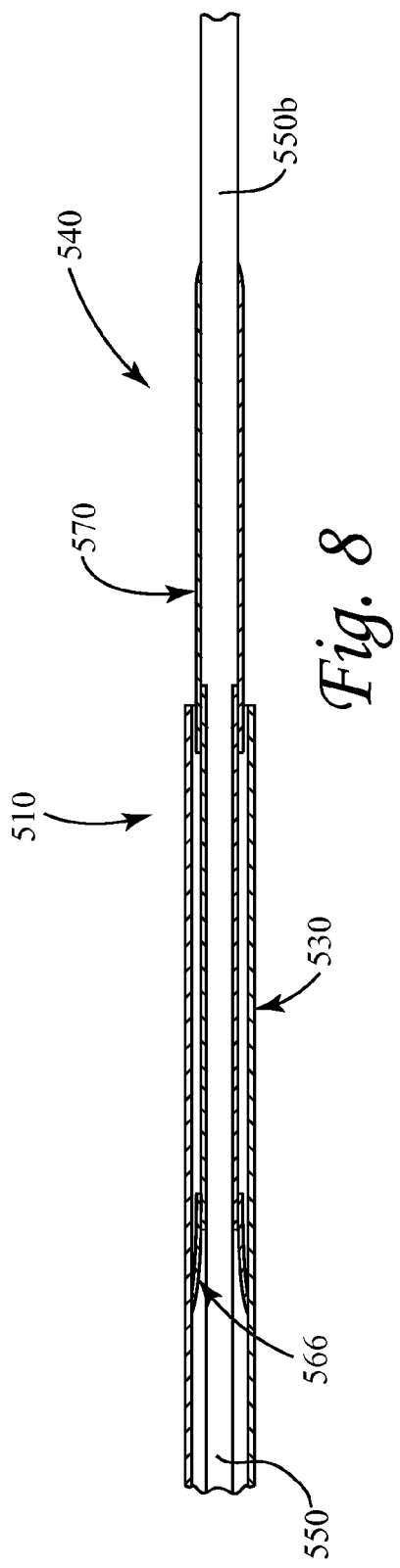
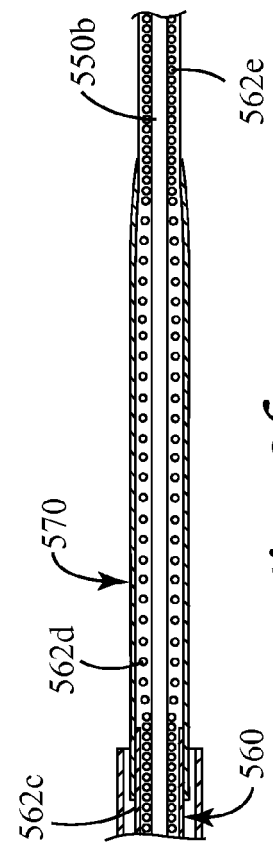
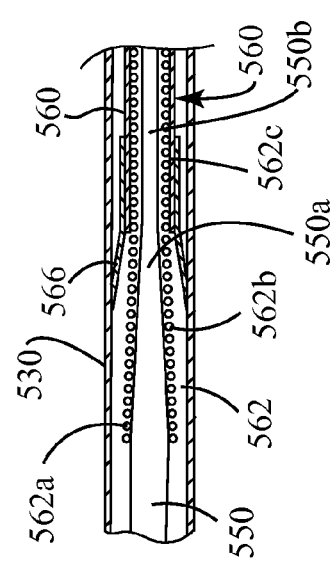

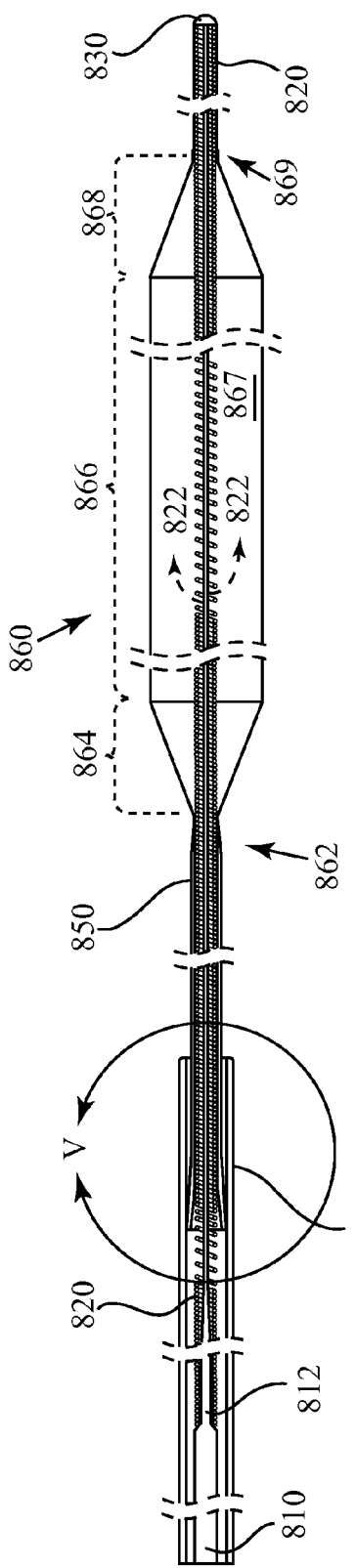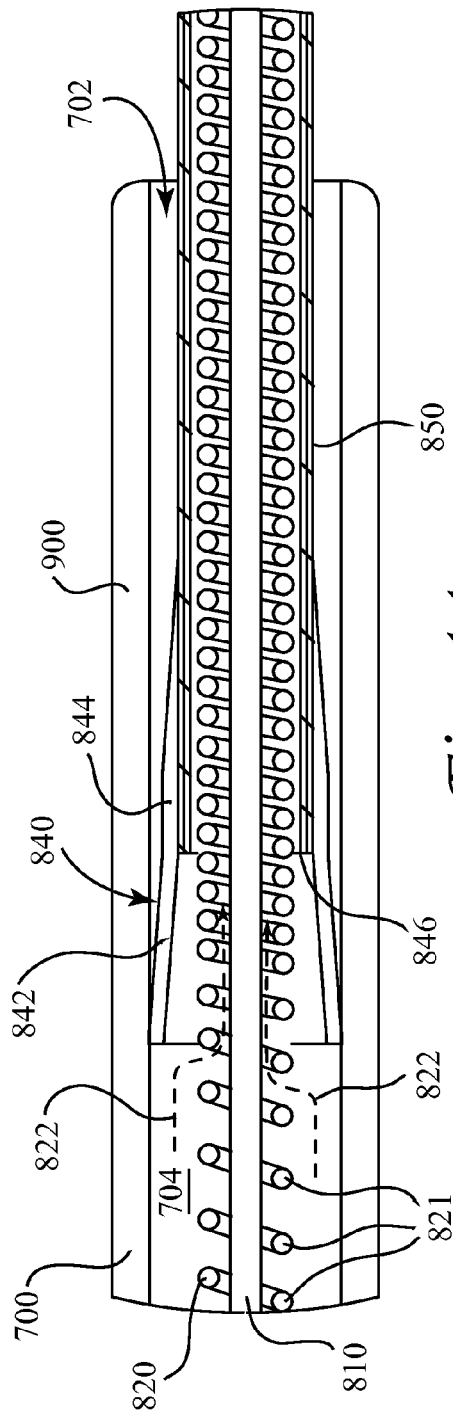

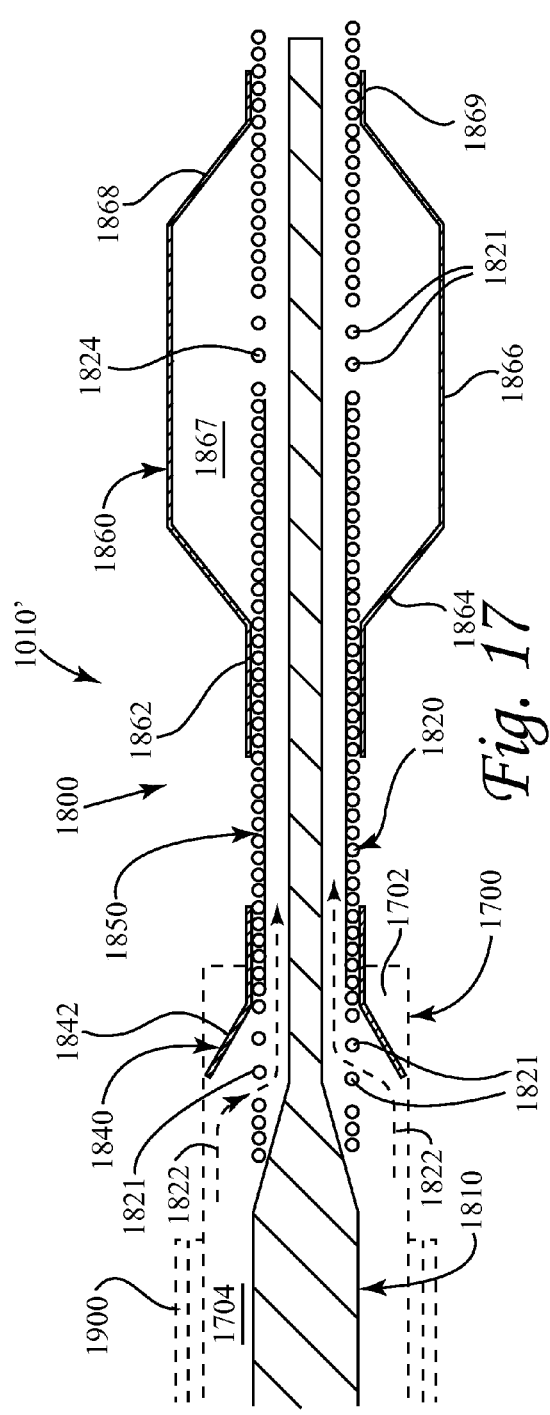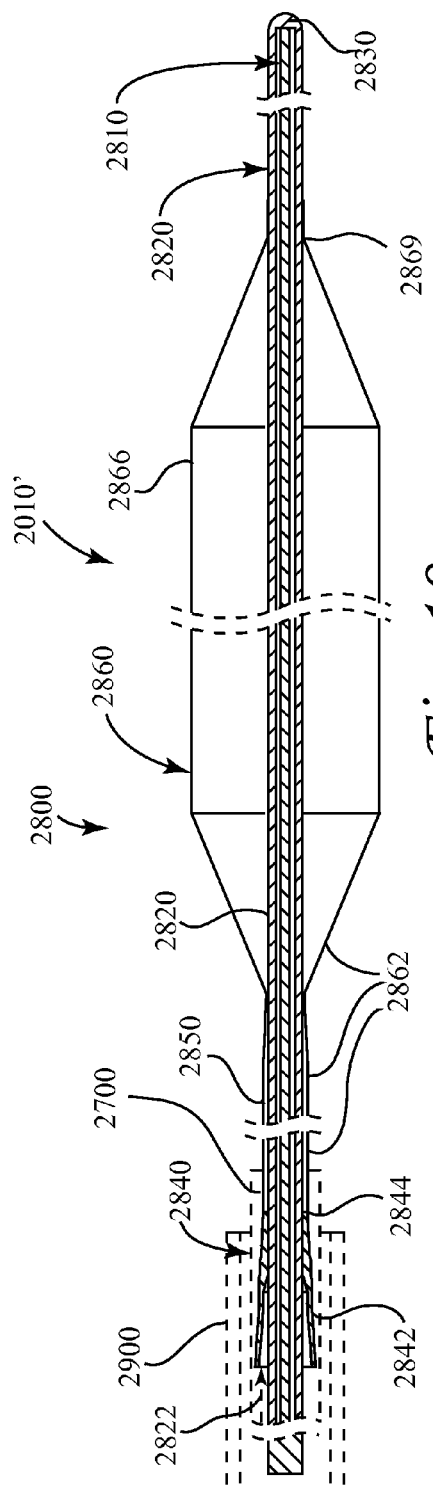

GUIDEWIRE AND CATHETER SYSTEM AND METHOD FOR TREATING A BLOOD CLOT

CROSS-REFERENCE TO RELATED APPLICATIONS

This application relates to U.S. patent application Ser. No. 14/111,051, filed May 13, 2014, which is the national stage of International Patent Application No. PCT/US11/43984, filed Jul. 14, 2011, which claims priority to U.S. Provisional Application 61/365,147, filed Jul. 16, 2010, the entire contents of each of which are incorporated by reference herein.

This application also relates to U.S. patent application Ser. No. 14/211,868, filed Mar. 14, 2014, which claims priority to U.S. Provisional Application 61/782,482, filed Mar. 14, 2013, the entire contents of each of which are incorporated by reference herein.

BACKGROUND

1. Field of the Invention

This invention relates broadly to systems and methods for treating an artery or vein of a patient. More particularly, this invention relates to systems and methods for treating blood clots and atherosclerosis in the brain and peripheral vessels of a patient, although it is not limited thereto.

2. State of the Art

A stroke is caused by a rupture or an occlusion of a blood vessel which leads to oxygen deprivation in the brain. In the United States, nearly eight hundred thousand people suffer a stroke each year, and over one hundred and forty thousand people die from strokes each year. Stroke is the leading cause of serious, long-term disability in the United States and the third leading cause of death. Approximately three-quarters of strokes in the United States are first attacks and approximately one-quarter are recurrent attacks. Eighty seven percent are ischemic in nature, meaning that they are caused by a restriction, obstruction, or blockage in the blood supply of the patient, and thirteen percent are hemorrhagic, meaning that they are caused by excessive bleeding. The economic cost of stroke to the United States is over forty billion dollars per year. The direct costs of medical care and therapy are almost thirty billion dollars per year.

It is well known in the art that the extent to which treatment of a stroke is successful in preventing death and/or in reducing the consequent damage to a patient is largely influenced by the time that elapses between the onset of the stroke and the proper treatment of the stroke. The elapsed time is a function of not only whether or not a patient is able to get to a medical facility or hospital, but also the nature of the stroke and whether or not the particular medical facility or hospital to which the patient is initially brought is best equipped to treat the stroke. The capability of the medical facility to treat the particular stroke may not be known until the patient is properly evaluated and analyzed. Generally, if more than three hours elapse between the onset of the stroke and treatment, then a combination of tPA (Tissue Plasminogen Activator—a drug used to dissolve blood clots) and mechanical treatments need to be utilized.

If a cerebral clot is diagnosed and removed within four hours of the clot's formation, a patient generally has a better chance to recover fully. If a neurointerventionist happens to be present (most are generally located at stroke centers), then certain devices may be available to remove the cerebral clot. One device is the Merci retrieval device made by Concentric Medical. With the Merci device, a small catheter (e.g., having a 0.015" inner diameter) is advanced through the femoral artery and fed up to the brain. A special Nitinol wire is advanced through the catheter to the clot. The wire changes form after passing through the clot and can be used to pull out the clot. A second device, sold by Penumbra, Inc. also uses a small catheter which is advanced through the femoral artery and fed up to the brain, but instead of pulling the clot out mechanically, utilizes suction to pull out the clot. Both of these devices are often unsuccessful in their intended functions.

Peripheral vascular disease (PVD) is a slow and progressive circulation disorder. It may involve disease in any of the blood vessels outside of the heart and diseases of the lymph vessels—the arteries, veins or lymphatic vessels. Organs supplied by these vessels such as the brain, heart, and legs, may not receive adequate blood flow for ordinary function. However, the legs and feet are most commonly affected; thus the name peripheral vascular disease. PVD includes a group of diseases in which blood vessels become restricted or blocked.

Venous thrombosis is the term used to describe a blood clot (thrombus) in a vein of the body. Most commonly these thrombi are found in the veins of the lower extremities. Thrombi found in veins deep in thighs or calves give rise to a condition called "deep vein thrombosis" (DVT). Venous thrombosis can occur in healthy as well as sick individuals. A complication most commonly associated with venous thrombosis is the condition known as "pulmonary embolism." A pulmonary embolus is actually a clot that has broken free from a vein wall and has traveled to the pulmonary artery, and then, if not removed, to a lung. When an embolus blocks a blood vessel in the lung, breathing is compromised and death may ensue. Accordingly, early treatment of DVT is desirable.

Other conditions associated with PVD that affect the veins include varicose veins, and chronic venous insufficiency. Lymphedema is an example of PVD that affects the lymphatic vessels. PVD is a progressive disease that can lead to gangrene of the affected area. PVD may also occur suddenly if an embolism occurs or when a blood clot rapidly develops in a blood vessel already restricted by an atherosclerotic plaque, and the blood flow is quickly cut off.

Various medical procedures or surgeries are recommended treatments for treating atherosclerosis and blood clots in peripheral vessels of a patient. But current treatments for relatively smaller vessels having atherosclerosis and/or blood clots are limited. These treatments may include angioplasty and vascular surgery.

SUMMARY

Systems and methods for treating a blood vessel in a patient are provided. The systems include a catheter/guidewire assembly adapted to be inserted in an artery or vein of the patient. The catheter/guidewire assembly includes an optional aspiration catheter, a microcatheter insertable through the aspiration catheter when provided, and a guidewire subassembly. The guidewire subassembly includes a guidewire which extends through the microcatheter, a coil element (also called a "support element" in some embodiments) which is affixed to the guidewire, and an optional balloon which may be a weeping or microjet balloon (i.e., a balloon with one or more small holes) which is affixed to the outside of the support element.

In one embodiment the support element includes a proximal tubular section which is affixed to the guidewire, a first helical (coiled) section which is loose around the guidewire, a second tubular section which supports the proximal end of the balloon and is loose around the guidewire, a second helical section which extends through the balloon, and a distal third tubular section which is also affixed to the guidewire and to which the distal end of the balloon can be attached. The proximal end of the balloon may include a flared portion which contacts the inner wall of the microcatheter. With the guidewire subassembly arranged in this manner, infusate which is injected through the microcatheter is prevented from exiting the distal end of the microcatheter by the flared portion of the balloon and will instead enter the support element at its first helical section. From there, the infusate will flow between the guidewire and the support element and out of the support element at its second helical section and into the balloon. The infusate will inflate the balloon, and when the infusate pressure reaches a desired level, the infusate will weep through the pores of the balloon.

In one embodiment, a cage element is provided around the balloon. The proximal end of the cage element may be attached to the balloon where the balloon attaches to the support element. Alternatively, the proximal end of the cage element may be attached to the distal end of the microcatheter. In one embodiment, the distal end of the cage element is attached to either the distal end of the support element or to the guidewire or may be attached to the balloon where the balloon attaches to the support element. In another embodiment, the distal end of the cage element is unattached to the catheter/guidewire assembly. According to one aspect, the cage element is arranged to restrain expansion of the balloon. According to another aspect, the cage element is arranged to remain open after balloon inflation in order to keep the clot open and allow blood to flow to the vessels that were affected by the clot. In this sense, the cage acts as a removable stent.

In another embodiment, a system for treating a blood clot consists of a microcatheter extending through an optional aspiration catheter, and a guidewire subassembly extending through and beyond the microcatheter. The guidewire subassembly includes (1) a guidewire core having at least one narrowed portion extending at or near the distal end of the guidewire, (ii) a coil element coupled to and extending around the narrowed portion of the guidewire core, the coil element defining at least one helical inlet opening along a portion of its length opening into a fluid flow path defined between the guidewire core and the coil element and at least one helical outlet opening spaced from and distal of the inlet opening, and (iii) a conical seal interposed between the coil and the microcatheter for sealing therebetween and ensuring that infusate within the microcatheter is directed into the blood vessel by traveling from the microcatheter, through the at least one helical inlet opening, then through the coil element and out of the helical outlet opening. In one embodiment, a balloon can surrounds the coil element at the helical outlet opening such that the balloon is inflated by the infusate. The balloon may be a weeping balloon.

In one embodiment the catheter/guidewire assembly is a relatively short assembly and is intended for insertion through the carotid artery. In another embodiment the catheter/guidewire assembly is a relatively longer assembly and is intended for insertion through the femoral artery. In another embodiment, the catheter/guidewire is sized to be inserted using a retrograde approach in a foot or other limb of a patient. In another embodiment, the catheter/guidewire is intended for insertion in the vein of a patient.

The assembly may be used as follows. First, a blood vessel such as the femoral or carotid artery or other artery or vein is punctured and a sheath inserted. A steerable guidewire is inserted into the sheath and steered until it crosses the location of interest—the location being described hereinafter with respect to a blood clot. The sheath is then removed, and the aspiration catheter of the described system is inserted through the puncture over the guidewire and up to just proximal the clot. The microcatheter of the described system is then fed between the aspiration catheter and the guidewire until it extends out of the aspiration catheter and into the clot. The steerable guidewire is then removed, and the guidewire subassembly of the described system with the guidewire, attached support element and balloon (if present) are inserted into the microcatheter until the balloon (if present) is located in the clot (with the distal end of the guidewire typically extending past the clot), or until the outlet openings in the coil are located in the clot. Alternatively, the guidewire subassembly may be used initially to function in place of the steerable guidewire, thereby eliminating the need for the steerable guidewire and reducing the number of insertion steps. Infusate (e.g., tPA alone or in combination with a radiopaque contrast agent) is then injected into the microcatheter, enters the coil (support element) at the inlet openings, flows between the guidewire and the coil and out of the coil at the outlet openings and into the clot or into the balloon (if present). If a balloon is present, sufficient pressure is applied to the infusate to inflate the balloon and cause the infusate to either weep or jet out of the pores of the balloon (depending upon force applied to the infusate) and into the clot or into the walls of the blood vessel. With a contrast agent, the expansion of the balloon (if present) and the flow of the infusate within the occluded vessel can be monitored in real-time. When sufficient infusate has been introduced into the clot or vessel walls, the pressure is removed to deflate the balloon (if present), and the microcatheter and guidewire subassembly are removed from the aspiration catheter. It is anticipated that the tPA in the infusate may completely lyse and dissolve the clot to effect recanalization, rendering subsequent aspiration of the clot unnecessary. However, if necessary suction may then be applied to the aspiration catheter in order to remove the clot. The aspiration catheter is then removed and the blood vessel is closed.

There are several methods currently being used by physicians for intravascular treatments that can be used in conjunction with the microcatheter/guidewire of the invention to effect re-canalization. A guiding catheter can be used as an initial support for the microcatheter/guidewire. If the guiding catheter cannot get close enough to the clot, another "aspiration catheter" is used, which is more flexible and able to track more distal. Then the microcatheter/guidewire is inserted. Also, physicians can group the aspiration catheter and microcatheter/guidewire devices together as a system and insert the system up to the vasculature. The microcatheter/guidewire is then fed to the clot. In all methods, aspiration, when performed, may be performed through the catheter that is closest to the clot.

Objects and advantages of the invention will become apparent to those skilled in the art upon reference to the detailed description taken in conjunction with the provided figures.

BRIEF DESCRIPTION OF THE DRAWINGS

FIG. 1b is a transparent perspective view of the embodiment of FIG. 1 in an inflated position.

FIG. 1c is broken, transparent side view of FIG. 1b.

FIG. 2 is a transparent perspective view of a second embodiment of the invention.

FIG. 2a is a broken, transparent side view of the embodiment of FIG. 2.

FIG. 2b is a transparent perspective view of the embodiment of FIG. 2 in an inflated position.

FIG. 2c is a broken, transparent side view of FIG. 2b.

FIG. 2d is a broken, transparent side view of the embodiment of FIG. 2 with the cage expanded and the balloon collapsed.

FIG. 3 is a transparent perspective view of a third embodiment of the invention.

FIG. 3a is a broken, transparent side view of the embodiment of FIG. 3.

FIG. 3b is a broken, transparent side view of the embodiment of FIG. 3 in an inflated position.

FIG. 3c is a broken, transparent side view of the embodiment of FIG. 3 with the cage expanded and the balloon collapsed.

FIG. 4 is a broken side view of a distal portion of the third embodiment of the invention, showing an alternative cage and balloon construction.

FIG. 5 is a broken side view of a distal portion of the third embodiment of the invention, showing another alternative cage and balloon construction.

FIG. 8 is a schematic longitudinal section view of a sixth embodiment of the invention.

FIGS. 8a and 8b are enlarged views of portions of FIG. 8.

FIG. 13 is a fragmentary, cross-sectional view of the system of FIG. 12 along section line IV-IV.

FIG. 14 is a fragmentary, further enlarged, cross-sectional view of a proximal section of a distal portion of the system of FIG. 13 within section circle V.

FIG. 17 is a fragmentary, enlarged, longitudinal cross-sectional view of a ninth embodiment of a guidewire system within a guiding catheter and with an optional balloon in an inflated condition.

FIG. 18 is a fragmentary, further enlarged, longitudinal cross-sectional view of a portion of a tenth embodiment of a guidewire system within a guiding catheter and with an optional balloon in an inflated condition.

Figure 1:
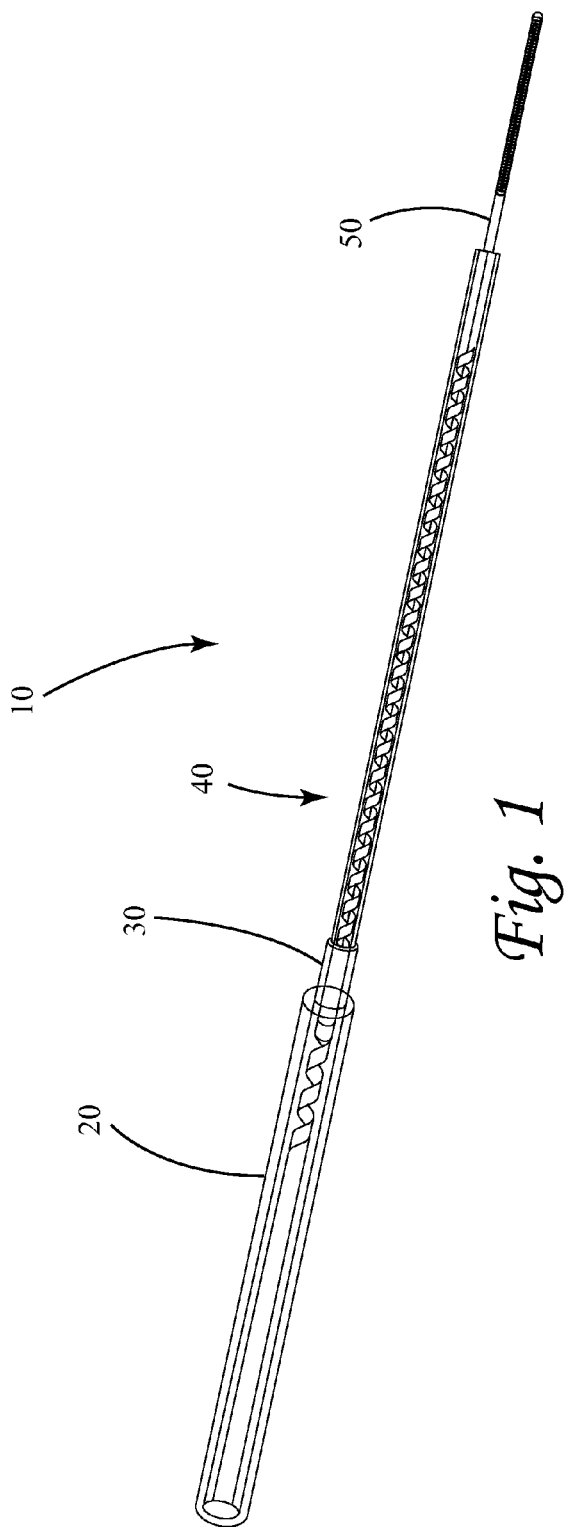
FIG. 1 is a transparent perspective view of a first embodiment of the invention.
Figure 1A:
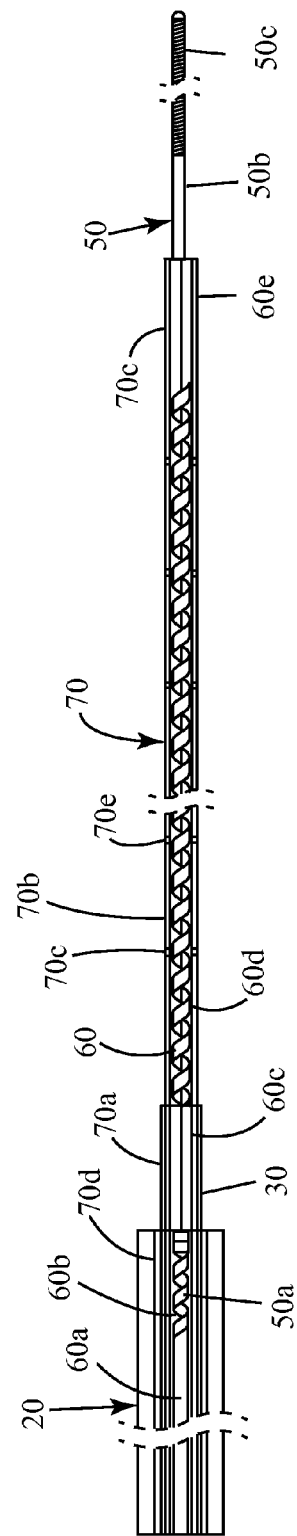
FIG. 1a is a broken, transparent side view of the embodiment of FIG. 1.
Figure 1D:
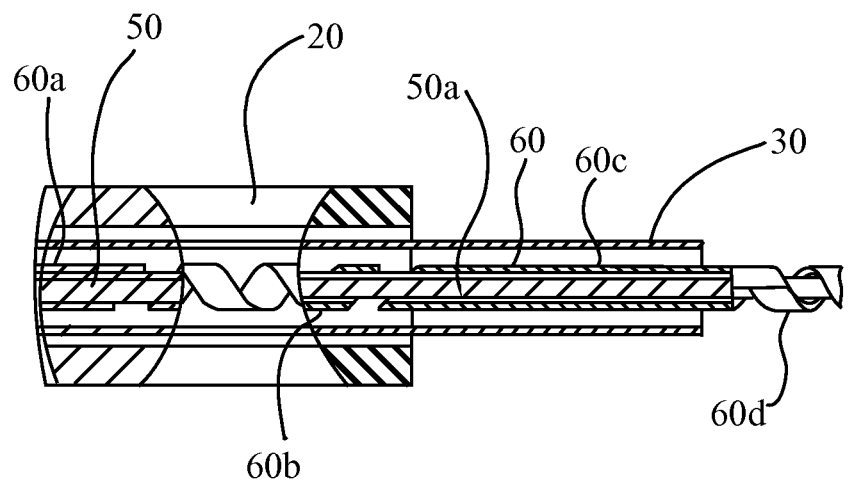
FIG. 1d is a partially transparent side view and partially cross-sectional view of a portion of the embodiment of FIG. 1 without the balloon.
Figure 1E:
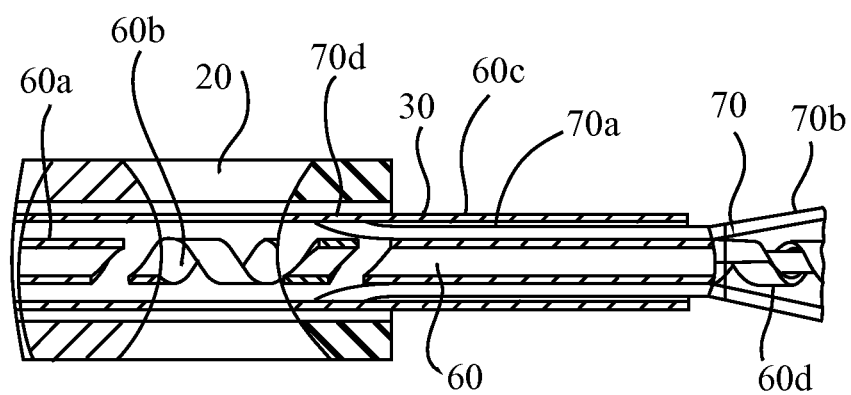
FIG. 1e is a partially transparent side view and partially cross-sectional view of the same portion of the embodiment shown in FIG. 1d but with the balloon and without the core wire.

The Figures are not necessarily drawn to scale.

DETAILED DESCRIPTION

For purposes of this disclosure, the terms "proximal" and "distal" are referenced relative to the hand of the operator of the guidewire and catheter system when the system is in use, as well as the site at which the system is inserted into the patient's body; system components and anatomical structure closer to the operator's hand and insertion site are considered relatively "proximal", whereas system components and anatomical structure further from the operator hand and insertion site are considered relatively "distal".

For purposes of this disclosure the term "plurality" is defined as "two or more than two." The term "another," as used herein, is defined as "at least a second or more." The terms "including" and/or "having" are defined as "comprising" (i.e., open language). The term "coupled" is defined as "connected, although not necessarily directly, and not necessarily mechanically."

For purposes of this disclosure, the term "about" or "approximately" applies to all numeric values whether or not explicitly indicated. These terms refer to a range of numbers that one of skill in the art would consider equivalent to the recited values (i.e., having the same function or result). In many instances, these terms may include numbers that are rounded to the nearest significant figure. It is further noted that the terms "about" and "approximately" include a range within ±20% of the value which follows the word "about" or "approximately."

Turning to FIG. 1 and FIGS. 1a-e, a first embodiment of a catheter/guidewire system 10 is seen for treating blood clots in the intracranial vasculature of a patient. System 10 includes an aspiration catheter 20, a microcatheter 30, and a guidewire subassembly 40. Aspiration catheter 20, which may be a guiding catheter or other support catheter, is approximately 120 cm-160 cm in length if it is to be introduced through the femoral artery, or approximately 20 cm-40 cm in length if it is to be introduced through the carotid artery, and has an inner diameter of between 0.040 and 0.060 inches and an outer diameter of between 0.06 and 0.10 inches. The microcatheter 30 may be slightly longer than the aspiration catheter 20 and insertable through the aspiration catheter. The microcatheter 30 may have an inner diameter of between 0.020 and 0.030 inches and an outer diameter of 0.023-0.033, with a wall thickness of approximately 0.003 inches. The microcatheter may be formed from a plastic extrusion with a stainless steel coil or braid. The guidewire subassembly 40 may be slightly longer than the microcatheter 30 and insertable through the microcatheter. The guidewire subassembly 40 includes a guidewire 50, a support element 60 (also called a "coil element" and a "fluid transport element", and a weeping or microjet balloon 70. As will be described in more detail hereinafter, a proximal end 60a of the support element 60 attaches to the guidewire 50.

Guidewire 50 may have a diameter of between 0.012 and 0.018 inches along most of its length. As is seen best in FIG. 1d, just distal the point of attachment of the support element 60 to the guidewire 50, the guidewire portion 50a has a decreased diameter in order to permit infusate flow between the guidewire portion 50a and the support element 60 as described hereinafter. The very distal end 50b of the guidewire may also decrease in diameter down to approximately 0.004-0.006 inches in diameter and terminates in a coil 50c. The distal end of the guidewire 50b may or may not be exposed. In other words, the coil 50c may butt up against the distal end 60e of the support element 60 such that the tip of the guidewire assembly has the same diameter as the proximal end of the guidewire, with only a coil exposed. The guidewire may be formed from stainless steel, Nitinol, or from another very flexible material.

The support element 60 of the guidewire subassembly may be a thin tube having helical cut-outs formed or cut in large portions thereof. Alternatively, the support element is formed from a helical coil having open wound portions. More particularly, support element may include a small proximal affixation portion 60a having an inner diameter that is substantially equal to or less than the outer diameter of the main length of the guidewire core wire 50. The proximal end 70a of the balloon (balloon neck) sits on top of the support element. Although not required, the combined diameter of the proximal fixation portion 60a of the support element and the thickness of the balloon neck may be arranged so that it does not exceed the diameter of the main length of guidewire. The affixation portion 60a may be tubular (although it could have holes and could be helical) and is affixed to the guidewire by soldering, brazing, welding, gluing, or other fixing techniques known in the art. Distal the affixation portion 60a of the support element is a first helical or coil portion 60b which loosely surrounds the decreased diameter portion 50a of the guidewire, and includes at least one (inlet) opening (e.g., a helical opening) thereby permitting infusate to enter the support element and to flow between it and the guidewire portion 50a. The coil portion 60b terminates in a small balloon support portion 60c which may be tubular and to which a proximal end portion (balloon neck) 70a of balloon 70 is attached by glue or by other well-known techniques to its outside surface. In this manner, support element 60 runs inside balloon 70. Distal the support section 60c, support element 60 has a second helical or coil portion 60d which is located inside the balloon 70, having at least one (outlet) opening thereby permitting infusate to exit the support element and enter the balloon 70. As seen in FIG. 1c, the second helical or coil portion 60d of support element 60 can extend entirely through the balloon 70, or can include a closed wall tubular construct as one or more portions of the second portion 60d. Regardless, the distal end of the support element may include a small tubular support portion 60e to which the distal end 70b of balloon 70 is attached, thereby preventing infusate from exiting from between the balloon 70 and the support element 60. Tubular support portion 60e is attached to the guidewire 50 to likewise prevent infusate from exiting the support element 60. The support element may be formed from Nitinol or stainless steel. If desired, portions 60a and 60e of the support element 60 can be made of or coated with a material such as platinum-iridium which under fluoroscopy can be used to help locate the position of the guidewire assembly. Because the large majority of support element 60 may be cut as a helix or coil, support element 60 is very flexible and does not affect the flexibility of the portion of the guide wire 50 extending within the balloon.

Balloon 70 has a proximal portion 70a attached to tubular support portion 60a of support element 60, a distal portion 70b attached to tubular support portion 60e of the support element 60, and an expandable middle portion 70c that extends around support element 60. The proximal portion 70a includes a proximal seal 70d (seen best in FIG. 1e) which is not directly attached to the support element 60 and which flares out to an outer diameter slightly larger than the inner diameter of the microcatheter 30 such that the seal 70d is always under compression by the inner surface of the microcatheter and prevents infusate from exiting the distal end of the microcatheter. The expandable middle portion 70c of the balloon 70 may include one or more microholes or pores 70e, each, in one embodiment, not exceeding a diameter of 0.002 inch, which permit infusate to escape out of the balloon when sufficient pressure is applied (e.g., in one embodiment less than 760 Torr above blood pressure and in another embodiment less than 400 Torr above blood pressure). The balloon may be a weeping balloon, in which the microholes or pores of sufficient dimension and/or number, and wherein appropriate pressure is applied to the infusate, to cause the infusate to weep or seep out of the balloon in a low pressure manner. Alternatively, the balloon may be a microjet balloon, with holes (or micropores) of size and number (e.g., one or more micropores) such that the infusate jets out of the balloon when the balloon is pressurized toward or in an expanded configuration. When a microjet balloon is employed, the clot is agitated by the force of the infusate jet to accelerate dissolution of the clot. A flow rate of 0.1 cc/sec of infusate through a balloon with two micropores (as shown in FIG. 4 described hereinafter) has been shown to be effective for achieving microjetting of the infusate, desired clot agitation, and clot dissolution. The balloon 70 may be made from silicon, polyurethane, latex, Kraton™ polymers (i.e., styrenic block copolymers consisting of polystyrene blocks and rubber blocks), or other materials suitable for use in a low pressure compliant balloon. Typically, the balloon is between 0.001 and 0.008 inches thick, between 0.4 and 0.8 inches long and is capable of having a nominal expanded diameter of no more than 0.18 inches. Balloon lengths will typically range from 0.2 up to 2 inches in length. Balloon 70 is seen in an inflated (expanded) state in FIGS. 1b and 1c and in a deflated (unexpanded) state in FIGS. 1 and 1a.

In one embodiment, the balloon of FIGS. 1a-1e may be an angioplasty-type balloon rather than a weeping balloon having holes or micropores.

The guidewire/catheter system 10 may be used as follows. First, either the femoral or carotid artery (not shown) is punctured and a sheath (not shown) inserted. A steerable guidewire (not shown) is inserted into the sheath and steered until it crosses the clot of interest (not shown). The sheath is optionally then removed, and the aspiration catheter 20 is then inserted through the sheath (if still present) and the puncture and over the guidewire and up to just proximal the clot (i.e., in one embodiment, it is not inserted through the clot). The microcatheter 30 is then fed between the aspiration catheter 20 and the guidewire until it extends out of the aspiration catheter and into the clot. The steerable guidewire is then removed, and the guidewire subassembly 40 with the guidewire 50, attached support element 60 and balloon 70 are inserted into the microcatheter 30 and snaked (extended) through the microcatheter until the balloon 70 is located within the clot (with the distal end 50b of the guidewire typically extending past the clot). Alternatively, the guidewire subassembly may be used initially to function in place of the steerable guidewire, thereby eliminating the need for the steerable guidewire and reducing the number of insertion steps. Infusate (e.g., tPA) is then injected into the microcatheter 30, enters the support element 60 at its first helical section 60b, flows between the reduced diameter guidewire portion 50b and the support element section 60b and out of the support element at its second helical section 60d and into the balloon 70. Sufficient pressure is applied to the infusate to inflate the balloon 70 and cause the infusate to weep out of the pores 70e of the balloon and into the clot or into the walls of the blood vessel (not shown). When sufficient infusate has been introduced into the clot or vessel walls, the pressure is removed, the balloon 70 deflates, and the microcatheter 30 and guidewire subassembly 40 may be removed from the aspiration catheter 20. Alternatively, one or more subsequent processes of infusion and inflation can be carried out prior to removal of the microcatheter and guidewire. Suction may then be applied to the aspiration catheter 20 in order to remove the clot. The aspiration catheter 20 is then removed and the artery (not shown) is closed. The design of the microcatheter 30 and guidewire subassembly 40, which allows construction of the elements with very small outer diameters, permits the system to be effectively used in smaller vessels than permitted with other known devices.

A second embodiment is seen in FIGS. 2 and 2a-2f. The second embodiment is similar in many respects to the first embodiment and is described in a manner where like parts are given like numbers which are one-hundred apart. Thus, system 110 includes an aspiration catheter 120, a microcatheter 130, and a guidewire subassembly 140, where the guidewire subassembly includes a guidewire 150, a support element 160, and a weeping or microjet balloon 170. All of these elements may be identical to, or substantially the same as their counterparts in the system 10 of FIGS. 1 and 1a-1e. System 110, however, further includes a balloon-deformable cage or stent 180. Cage 180 has a proximal end 180a which is optionally attached to a tubular cage tether 182 and a free distal end 180b which may be located proximal the distal end 170c of balloon 170. Where there is no cage tether, the proximal end 180a of the cage is affixed directly to the proximal end 170a of the balloon 170 (just distal the seal portion 170d) by gluing or affixing by other processes known in the art. Where there is a cage tether, the tubular cage tether 182 is glued or otherwise affixed to the proximal end 170a of the balloon 170.

As seen best in FIG. 2a, the cage 180 is chosen to have an inner diameter which either contacts the outer surface of the balloon or is just slightly larger than the outer surface diameter of the balloon when the cage (and balloon) is in an initial unexpanded position. As seen in FIGS. 2b and 2c, inflation of the balloon causes the middle portion 170b of the balloon to expand the cage to an expanded position. In addition, when the balloon is expanded, infusate may weep or jet out of the holes 170e located along the balloon. According to one aspect, the cage may be arranged so that it limits the ability of the balloon to expand beyond a certain diameter. This may be done by either designing the cage with a limited ability to expand, or by arranging the cage to provide a sufficient force when it reaches a particular diameter which would prevent the balloon from expanding. In technical terms, the resistive force (Fr) of the cage 180 is greater than or equal to the opening force of the balloon 170 for a given diameter (Fo). The balloon opening force will vary according to the number of and size of the infusate holes. The force limiting aspect of the cage can be broken down into two separate embodiments. If the material of the cage has a high tensile strength, e.g., spring steel, or is superelastic, e.g., Nitinol, the balloon will expand until Fr=Fo. The diameter will be a function of the respective forces (i.e. the cage and balloon design will have corresponding maximum diameters, e.g., 2 mm. When the balloon is deflated, the cage will return to a collapsed position. If the material of the cage is inelastic, e.g., annealed stainless steel, then when Fr=Fo and the diameter is achieved, the cage will remain in the expanded position even when the balloon is deflated, leaving a conduit for blood to flow. The cage can be removed by pulling the guidewire/microcatheter subassembly into the aspiration catheter, or retracting just the guidewire relative to the microcatheter.

As an alternative to a cage for controlling expansion of the balloon, the balloon may be constructed of a compliant material. The holes in the balloon may then function as a pressure relief; as the balloon expands, the holes get larger (in distinction from non-compliant balloons). As another alternative, a pressure relief can be provided within or coupled to the instrument to control and limit pressure. By way of example, an external pressure relief valve can be connected to a luer fitting on the hub of the microcatheter or to a Touhy-Borst valve, which is then connected to the hub of the microcatheter. As yet another alternative, the infusion rate can be controlled by the use of a flow restrictor.

The guidewire/catheter system 110 may be used as follows. First, either the femoral or carotid artery (not shown) is punctured and a sheath (not shown) inserted. A steerable guidewire (not shown) is inserted into the sheath and steered until it crosses the clot of interest (not shown). The sheath optionally may then be removed, and the aspiration catheter 120 inserted through the puncture over the guidewire and up to just proximal the clot. The microcatheter 130 is then fed between the aspiration catheter 120 and the guidewire until it extends out of the aspiration catheter and into or through the clot. The steerable guidewire is then removed, and the guidewire subassembly 140, comprising the guidewire 150, attached support element 160, balloon 170, and cage 180, is inserted into the microcatheter 130 and snaked through the microcatheter until the balloon 170 is located in the clot (with the distal end 150b of the guidewire typically extending past the clot). Infusate (e.g., tPA) is then injected into the microcatheter 130, enters the support element 160 at the inlet opening(s) of the first helical section 160b, flows between the reduced diameter guidewire portion 150b and the support element section 160b and out of the support element at the outlet opening(s) at its second helical section 160d and into the balloon 170. Sufficient pressure is applied to the infusate to inflate the balloon 170 and cause the infusate to weep or jet out of the pores 170e of the balloon and into the clot or into the walls of the blood vessel (not shown) as well as expanding the cage 180 so that the cage presses against the walls of the blood vessel. When sufficient infusate has been introduced into the clot or vessel walls, the pressure is removed, the balloon 170 deflates, and if the cage 180 is biased toward a collapsed position, the cage collapses. The microcatheter 130 and guidewire subassembly 140 are then removed from the aspiration catheter 120. Suction may then be applied to the aspiration catheter 120 in order to remove the clot. The aspiration catheter 120 is then removed, the sheath (if present) is removed, and the artery (not shown) is closed. It is noted that if the cage 180 is not biased toward a collapsed position, when the balloon 170 deflates, the cage remain in an expanded position. Pulling the guidewire subassembly 140 including the cage proximally into the microcatheter 130 or the aspiration catheter 120, or pushing the microcatheter 130 forward relative to the cage 180 will cause the cage to collapse, whereupon, the microcatheter 130 and guidewire subassembly 140 may be removed from the aspiration catheter 120. Suction may then be applied as previously described, and then the catheter 120 may be removed and the artery closed.

A third embodiment of the invention is seen in FIGS. 3 and 3a-3c. The third embodiment is similar in many respects to the second embodiment and is described in a manner where like parts are given like numbers which are one-hundred apart. Thus, system 210 includes an aspiration catheter 220, a microcatheter 230, and a guidewire subassembly 240, where the guidewire subassembly includes a guidewire 250, a support element 260, a weeping or jetting balloon 270, and a cage 280. All of these elements may be identical to, or substantially the same as their counterparts in the system 110 of FIGS. 2 and 2a-2d except that cage 280 has a distal end 280b which is affixed either to the distal end 260e of the support element 260, the distal end 270c of the balloon, or to the guidewire 250. Affixation of the distal end 280b of the cage 280 may be accomplished with the use of a second tubular cage tether 284 or by directly affixing the distal end of the cage to the balloon 270, support element 260 or to the guidewire 250. Similarly, and as in the second embodiment, the proximal end 280a of the cage 280 may likewise be affixed to the proximal end 270a of the balloon 270 either directly or via a tubular cage tether 282.

As seen best in FIG. 3a, the cage 280 is chosen to have an inner diameter which either contacts the outer surface of the balloon or is just slightly larger than the outer surface diameter of the balloon when the cage (and balloon) is in an initial unexpanded position. The cage 280 may be constructed of a braid of wires or other structural elements that extend from the proximal to distal ends of the balloon. Alternatively, as seen in FIG. 4, the cage 280' may be constructed to include a central ring 280b' formed by a series of Z-bends in a wire-form or from a laser-cut or stamp-cut form that is radially expansible. The central ring 280a' is coupled to a proximal portion 270a' and optionally a distal portion 270c' of the balloon 270 with a plurality of longitudinally arranged struts 280d' and non-expansible proximal and distal rings 280a' and 280c', which may also be formed from a series of Z-bends. Optionally additional radially expansible rings (not shown) may be provided to the cage 280'. As yet another modification of the design, as shown in FIG. 5, the proximal end 280a'' of the cage 280'' may be integrated with the distal end of the microcatheter 230'' (rather than coupled to the proximal end 270a'' of the balloon 270'', as previously described). In such a configuration, the cage essentially has a common diameter with the microcatheter. Also, in such a configuration, the distal end of the cage is not attached to the distal end of the balloon 270''. However, even though not attached to the balloon 270'', when the balloon 270'' is expanded, the middle portion of the cage will expand accordingly.

Referring back to FIG. 3b, inflation of the balloon causes the middle portion 270b of the balloon to expand the cage (all described designs) to an expanded position. In addition, when the balloon is expanded, infusate may weep or jet out of the holes 270e located along the balloon. Referring again to FIGS. 4 and 5, jetting is facilitated with fewer holes, such as the two holes 270e' of balloon 270', which may be longitudinally spaced along the length of the balloon one-third the balloon-length in from the proximal end and one-third the balloon-length in from the distal end of the balloon (FIG. 4), or one hole 270e'' of balloon 270'' (FIG. 5).

According to one aspect, the cage may be arranged so that it limits the ability of the balloon to expand beyond a certain diameter. This may be done by either designing the cage with a limited ability to expand, or by arranging the cage to provide a sufficient force when it reaches a particular diameter that would prevent the balloon from expanding. According to another aspect, the cage may be arranged so that it does not significantly impact the expansion of the balloon, and the cage 280 will expand to whatever diameter the balloon 270 (FIG. 3b), 270' (FIG. 4), 270'' (FIG. 5) expands. According to another aspect, and as seen in FIG. 3c, the cage 280 may be arranged so that when the balloon 270 deflates after it has been inflated, the cage remains expanded. If the cage is arranged to remain expanded, movement of the microcatheter 230 distally relative to the cage will cause the cage to collapse inside the microcatheter or retraction of the guidewire/microcatheter assembly into the aspiration catheter will cause the cage to collapse (assuming the expanded diameter of the cage is larger than the inner diameter of the aspiration catheter). According to a further aspect, the cage 280 may be spring biased toward a closed position such that when the balloon is no longer being inflated by infusate, the cage 280 will return to a collapsed position. The guidewire/catheter system 210 may be used in the same manner as the guidewire/catheter system 110 of FIGS. 2 and 2a-2d.

As alternate to the above described arrangement, the support for the balloon is two discrete and longitudinally displaced sections. A first section includes a proximal portion attached to the guidewire, a helical portion extending from the proximal portion, and a first support portion extending from the helical portion. The second section is coupled to the guidewire, and the distal end of the balloon is coupled to the second section. The location and coupling of the second section may be the same as described above with respect to the guidewire 50, tubular support portion 60e, and the balloon 70 (FIGS. 1 and 1c). In this arrangement, no section of the balloon support, helical or otherwise, extends continuously through the balloon.

Figure 6:
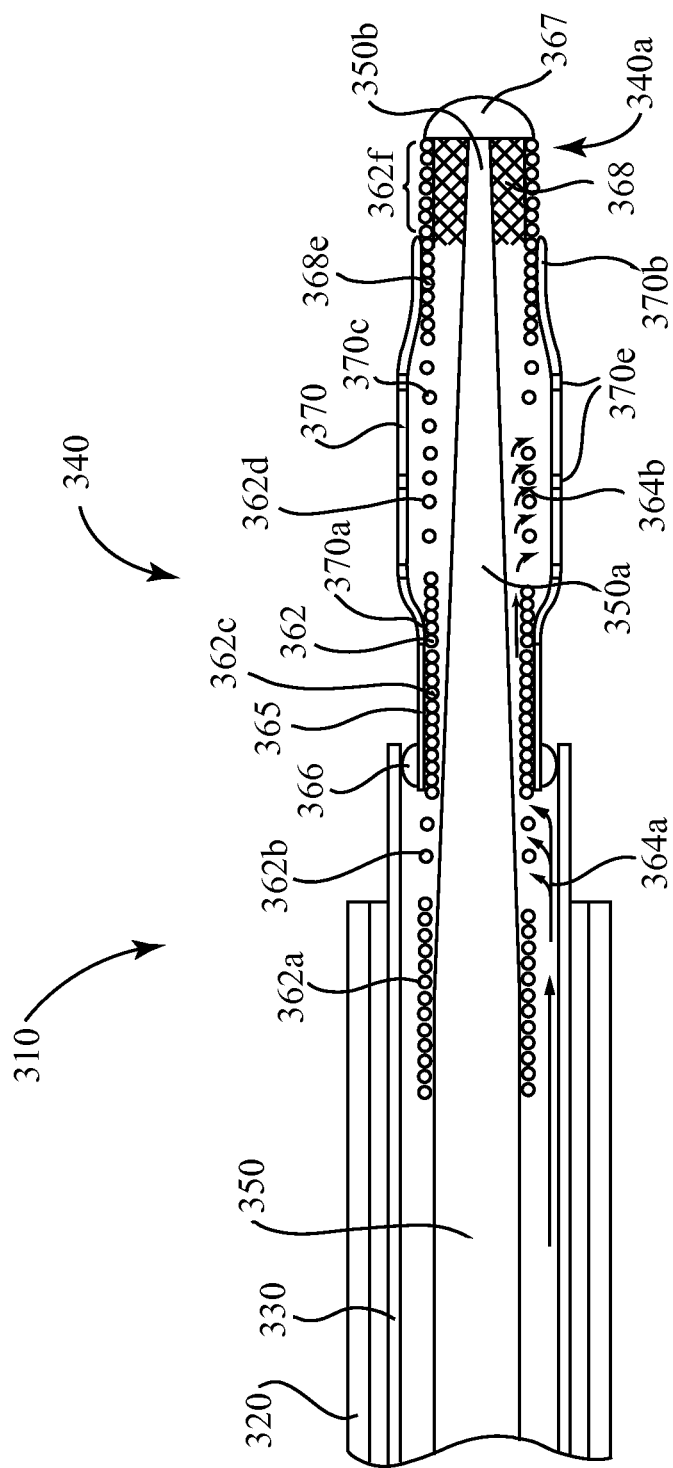
FIG. 6 is a schematic longitudinal section view of a fourth embodiment of the invention.

Turning now to FIG. 6, a fourth embodiment is seen. The fourth embodiment is similar in many respects to the first embodiment and is described in a manner where like parts are given like numbers. Thus, system 310 includes an aspiration catheter 320, a microcatheter 330, and a guidewire subassembly 340. The aspiration catheter and microcatheter may be identical to, or substantially the same as their counterparts in the system 10 of FIGS. 1 and 1a-1e. The guidewire subassembly 340 of system 310, however, is different including a guidewire core 350, a helical wound coil element 362, and a weeping or microjet balloon 370.

The guidewire core 350 may be constructed of a wire having a diameter of approximately 0.014 inches from its proximal end to a distal tapering diameter portion 350a. The tapering diameter portion 350a may be approximately 1 to 3.3 inches in length, and the guidewire core tapers down to approximately 0.003 inches at or adjacent its distal tip 350b.

The balloon 370 is made from a polymer that may have a material thickness of approximately 0.002 to 0.008 inches. Infusate is permitted to flow between the tapering diameter portion 350a of the guidewire 350 and the helical coil element 362 and into the balloon 370 as described hereinafter.

The coil element 362 extends over the tapering diameter portion 350a of the guidewire. The coil element 362 is constructed of helically wound platinum/stainless steel or Nitinol wire, which may have a wire diameter of approximately 0.003 inches. In one embodiment, the coil element 360 includes (i) a tight pitch, closed wound first portion 362a that can have a length of approximately 0.2 to 0.7 inches, (ii) a loose pitch, open wound second portion 362b that can have a length of approximately 0.2 to 0.7 inches, (iii) a tight pitch, closed wound third portion 362c that can have a length of approximately 0.2 to 0.7 inches, (iv) a loose pitch, open wound fourth portion 362d that can have a length of approximately 0.2 to 0.7 inches, (v) a tight pitch, closed wound fifth portion 362e that can have a length of approximately 0.2 to 0.5 inches, and (vi) a loose pitch, open wound sixth portion 362f that can have a length of approximately 0.08 to 0.25 inches. The first portion 362a of the coil element is connected to the core wire 350 at or adjacent the proximal end of the tapering diameter portion 350a. The open wound second portion 362b of the coil element defines at least one opening that permits infusate within the microcatheter 330 to flow between the coil element and the tapering diameter portion 350a of the guidewire core 350 (as indicated by arrows 364a). The closed wound third portion 362c is coated with a polymeric thin layer 365, that can be approximately 0.001 to 0.003 inches in material thickness, that fluid seals the third portion 362c yet maintains the flexibility of the coil element 362. A ring seal 366, that may be formed as a bead of polymer on the proximal end of the third portion 362c, is in contact with the inner surface of the microcatheter and prevents infusate from exiting the distal end of the microcatheter 330. The proximal end 370a of the balloon 370 is bonded over the polymeric thin layer 365 or directly to the windings of the closed wound third portion 362c, and the distal end 370c of the balloon is bonded to the close wound fifth portion 362e. The open wound fourth portion 362d defines at least one outlet opening that permits infusate within the coil element to flow out of the coil element 362 and into the surrounding balloon 370 (as shown by arrows 364b). The distal ends of the core wire 350 and coil element 362 are provided with a blunt atraumatic tip 367 that may be integrally formed with the core wire 350. A polymer 368 is injected into the open wound sixth portion 362f of the coil element to permanently fluid seal the distal tip 340a of the guidewire subassembly 340.

The guidewire/catheter system 310 may be used as follows. First, either the femoral or carotid artery (not shown) is punctured and a sheath (not shown) inserted. A steerable guidewire (not shown) is inserted into the sheath and steered until it crosses the clot of interest (not shown). The sheath may then be removed, and the aspiration catheter 320 is inserted through the puncture over the steerable guidewire and up to just proximal the clot. The microcatheter 330 is then fed between the aspiration catheter 320 and the guidewire until it extends out of the aspiration catheter and into or through the clot. The steerable guidewire is then removed, and the guidewire subassembly 340, comprising with the guidewire 350, coil element 362, and balloon 370, is inserted into the microcatheter 330 and snaked through the microcatheter until the balloon 370 is located in the clot (with the distal end 350c of the guidewire typically extending past the clot). Alternatively, the guidewire subassembly may be used initially to function in place of the steerable guidewire, thereby eliminating the need for the steerable guidewire and reducing the number of insertion steps. Infusate (e.g., tPA) is then injected into the microcatheter 330, enters the open wound second portion 362b of the coil element 362, flows between the tapered diameter portion of the core wire 350a and the coil element 362, and into the balloon 370. Sufficient pressure is applied to the infusate to inflate the balloon 370 and cause the infusate to weep out of the pores 370e of the balloon and into the clot or into the walls of the blood vessel (not shown). When sufficient infusate has been introduced into the clot or vessel walls, the pressure is removed, and the balloon 370 deflates. The microcatheter 330 and guidewire subassembly 340 are then removed from the aspiration catheter 320. Suction may then be applied to the aspiration catheter 320 in order to remove the clot. The aspiration catheter 320 is then removed, the sheath (if present) is removed, and the artery (not shown) is closed.

Figure 7:
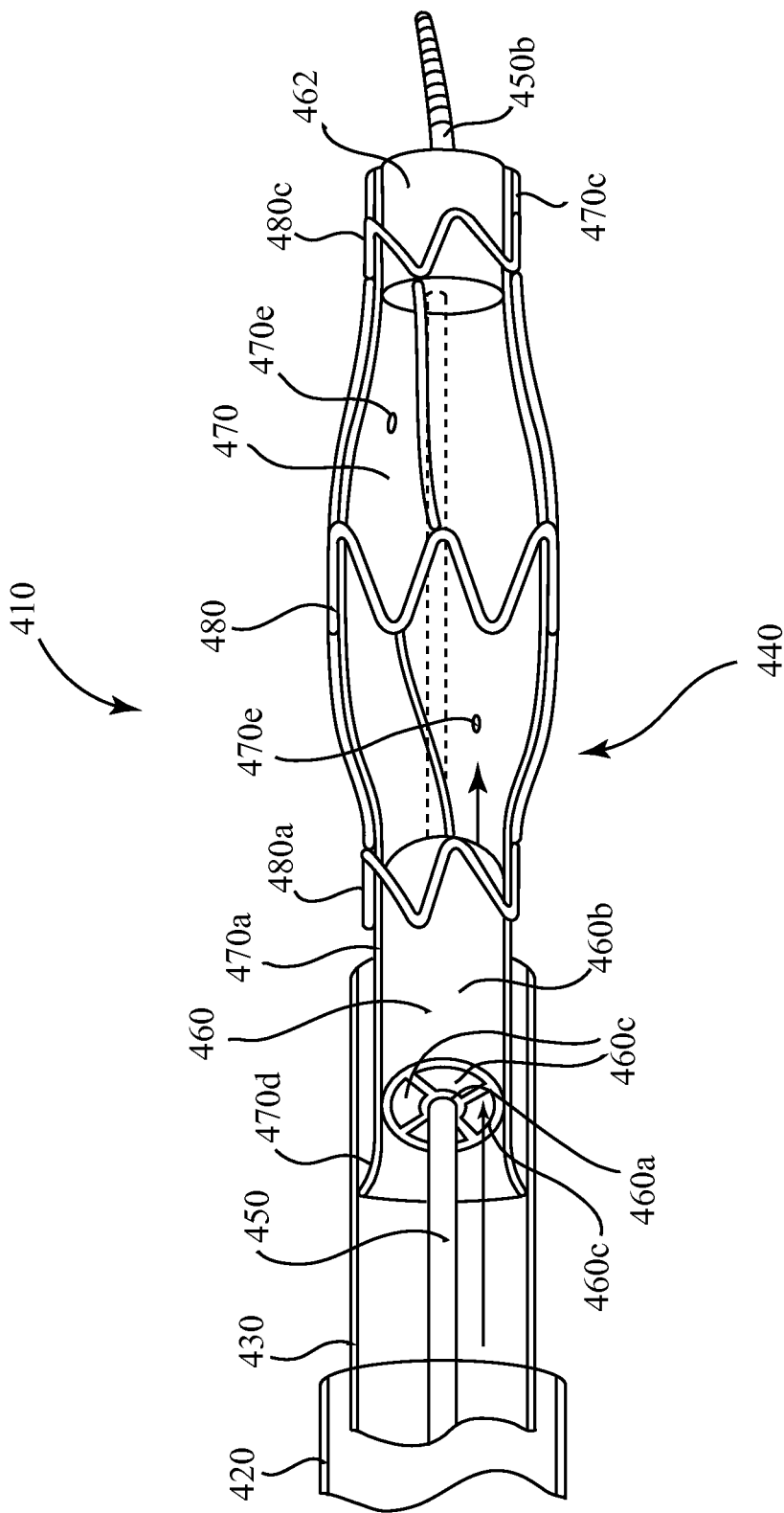
FIG. 7 is a broken, partial perspective and partial transparent side view of a fifth embodiment of the invention.

Referring to FIG. 7, a fifth embodiment of the invention is seen. The fifth embodiment is similar in many respects to the earlier embodiments and is described in a manner where like parts are given like numbers. Thus, system 410 includes an aspiration catheter 420, a microcatheter 430, and a guidewire subassembly 440. The aspiration catheter and microcatheter may be identical to, or substantially the same as their counterparts in the system 10 of FIGS. 1 and 1a-1e or system 310 of FIG. 6. The guidewire subassembly 440 of system 410, however, is different including a guidewire core 450, a hub 460, and a weeping or microjet balloon 470.

The guidewire core extends through the microcatheter 430 and through the balloon 470 of the subassembly 440. The guidewire core and balloon may be of any construction described in the earlier embodiments. However in distinction from the earlier embodiments, the core wire 450 extends through a hub 460 to which the proximal end of the balloon is affixed. The hub includes a central bore 460a through which the core wire 450 extends, an outer surface 460b which is in contact with the inner surface of the proximal end 470a of the balloon, and passageways 460c through which the infusate can flow from the microcatheter 430 to the interior of the balloon. The balloon includes a flared proximal opening 470d which contacts the inner surface of the microcatheter 430 to prevent infusate from leaking out of the microcatheter between the microcatheter and the balloon. The distal end of the balloon 470c is provided about a distal support 462 which is fixedly mounted at the distal end 450e of the core wire. When infusate is forced through the microcatheter 430, it travels through the passageways 460c, inflates the balloon 470 and then is directed out of the balloon through holes 470e and into contact with the clot. As described in the above embodiments, a self-expandable or pressure-expandable cage 480 is optionally provided over the balloon and operates to limit expansion of the balloon and/or temporarily maintain patency through the vessel after the balloon is deflated. The proximal end of the cage may be coupled over the hub 460, and the distal end of the cage may be coupled over the distal support 462.

The guidewire/catheter system 410 may be used as follows. First, either the femoral or carotid artery (not shown) is punctured and a sheath (not shown) inserted. A steerable guidewire (not shown) is inserted into the sheath and steered until it crosses the clot of interest (not shown). The sheath may then be removed, and the aspiration catheter 420 is inserted through the puncture over the steerable guidewire and up to just proximal the clot. The microcatheter 430 is then fed between the aspiration catheter 420 and the guidewire until it extends out of the aspiration catheter and into or through the clot. The steerable guidewire is then removed, and the guidewire subassembly 440, comprising with the guidewire 450, hub 460 and balloon 470, is inserted into the microcatheter 430 and snaked through the microcatheter until the balloon 470 is located in the clot (with the distal end 450b of the guidewire typically extending past the clot). Alternatively, the guidewire subassembly may be used initially to function in place of the steerable guidewire, thereby eliminating the need for the steerable guidewire and reducing the number of insertion steps. Infusate (e.g., tPA), which may be in combination with a fluoroscopic contrast agent, is then injected into the microcatheter 430, enters through the passageways 460c in the hub 460, and into the balloon 470. Sufficient pressure is applied to the infusate to inflate the balloon 470 and cause the infusate to weep or jet out of the holes 470e of the balloon 470 and into the clot or into the walls of the blood vessel (not shown). When a contrast agent is used, expansion of the balloon as well as the flow of the infusate out of the balloon is visualized with standard fluoroscopic equipment. As such, visualization of recannulization can be viewed in real-time. When sufficient infusate has been introduced into the clot or vessel walls, the pressure is removed, and the balloon 470 deflates. The cage, if provided, may then automatically collapse, or be moved against the distal end of one of the microcatheter 430 or aspiration catheter 420 to force its collapse. The microcatheter 430 and guidewire subassembly 440 are then removed from the aspiration catheter 420. Suction may then be applied to the aspiration catheter 420 in order to remove the clot. The aspiration catheter 420 is then removed, the sheath (if present) is removed, and the artery (not shown) is closed.

In an experiment using rabbits with induced blood clots in vessels of similar size to the human middle cerebral artery, a device as described with reference to FIG. 6 was shown to be effective in (1) delivering tPA directly within an occluding thrombus, (2) creating flow in the occluded vessel, and (3) resulting in an acceptable level of intimal/medial disruption. In the experiment, the device of the invention was delivered through a microcatheter, and the balloon was positioned within the clot. An infusion of the tPA Alteplase was mixed with a contrast agent in a 1:1 ratio and was infused from the distal to the proximal end of the clot. Multiple dilatations with the balloon were carried out with the inflation pressure monitored and kept between 760-1520 Torr. For comparison purposes, an angioplasty balloon was also positioned within a clot and multiple inflations were carried out from the distal to the proximal end, and a delivery microcatheter was positioned within a clot and the Alteplase dose diluted with saline in a 1:3 ratio which was infused from the distal to the proximal end of the clot. After the experiment it was concluded that with the device of the invention, Alteplase was able to be delivered directly within the occluding thrombus and achieve recanalization early and with a reduced thrombolytic dose in comparison with standard thrombolytic infusion techniques (delivery microcatheter) and mechanical disruption (balloon angioplasty) alone.

A sixth embodiment of the invention is seen in FIGS. 8, 8a, and 8b. The sixth embodiment is similar in many respects to the earlier embodiments and is described in a manner where like parts are given like numbers. Thus, system 510 includes an aspiration catheter (not shown), a microcatheter 530, and a guidewire subassembly 540. The aspiration catheter and microcatheter may be identical to, or substantially the same as their counterparts in the system 10 of FIGS. 1 and 1a-1e or system 310 of FIG. 6. The guidewire subassembly 540 of system 510, however, is different including a guidewire core 550, a helical wound coil element 562, a weeping or microjet balloon 570, an intermediate tube 560, and a seal 566.

As seen best in FIGS. 8a and 8b, the coil element 562 extends over the tapering diameter portion 550a of the guidewire. The coil element 562 is constructed of helically wound platinum/stainless steel or Nitinol wire. The coil element 560 includes (i) a tight pitch, closed wound first portion 562a (ii) a loose pitch, open wound second portion 562b, (iii) a tight pitch, closed wound third portion 562c, (iv) a loose pitch, open wound fourth portion 562d, and (v) a tight pitch, closed wound fifth portion 562e. A distal loose pitch, open wound sixth portion may be provided if desired. The first portion 562a of the coil element is connected to the core wire 550 at or adjacent the proximal end of the tapering diameter portion 550a. The open wound second portion 562b of the coil element permits infusate within the microcatheter 530 to flow between the coil element and the tapering diameter portion 550a of the guidewire core 550 (as in the arrangement of FIG. 6). The closed wound third portion 562c is coupled to the intermediate tube 560, and is of a diameter that permits the infusate to continue to flow between it and a reduced diameter portion 550b of the guidewire core 550. As seen best in FIG. 8a, the seal 566 is attached to the proximal end of the intermediate tube 560 and flares outwardly and over the coil element 562 as it extends proximally into contact with the inside of the microcatheter 530; while as seen best in FIG. 8b, the proximal end of the balloon 570 is attached to the distal end of the intermediate tube 560, and the distal end of the balloon is attached to the fifth wound tightly wound portion 562e of the coil. Tightly wound portion 562e of the coil is in turn attached to the reduced diameter portion 550b of the guidewire, so that infusate cannot flow past the distal end of the balloon. Instead, the fourth loosely wound portion 562d of the coil is located inside the balloon 570 and permits infusate which is flowing between the coil 52 and the guidewire 550 to flow outwardly in order to inflate the balloon 570 and, if the balloon is provided with pores, to weep or jet out of the pores of the balloon.

Optionally, the seal 566 may be made of polyurethane, the intermediate tube 560 made of polyolefin, and the balloon 570 made of a biocompatible elastomer such as Chrono-Prene (a trademark of AdvanSource Biomaterials Corp. of Massachusetts). The seal and intermediate tube can be joined by "welding" them together using heat and/or pressure. Likewise, the intermediate tube and balloon can be joined by "welding" them together using heat and/or pressure. In this manner, an effectively single element of different stiffnesses and functions is generated, with the intermediate tube being stiffer than the balloon and seal. Of course, other materials and connecting methods could be utilized.

The sixth embodiment of the guidewire/catheter system may be used in much the same manner as one or more of the previously described embodiments.

Figure 9:
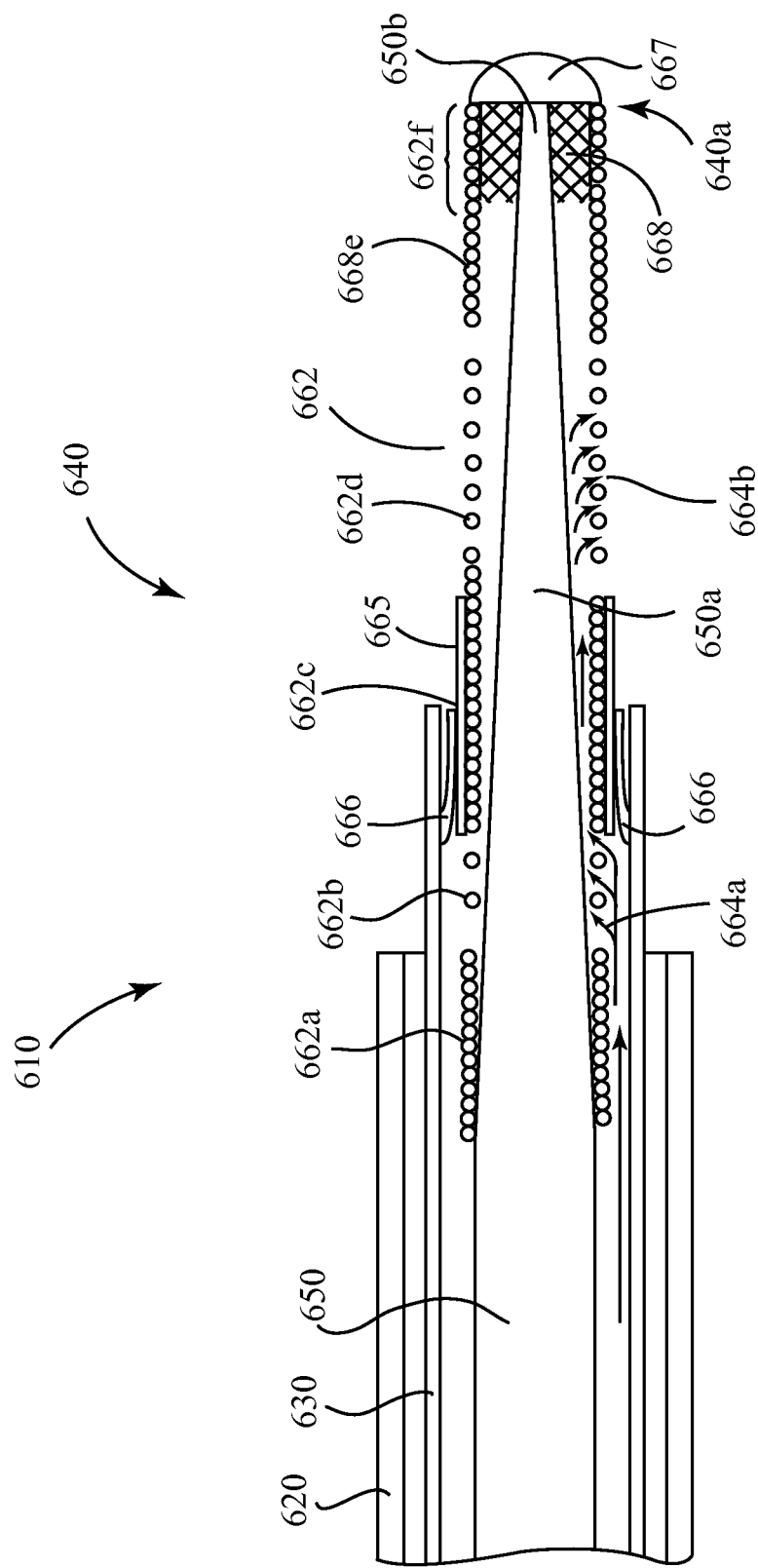
FIG. 9 is a schematic longitudinal section view of a seventh embodiment of the invention.

Turning now to FIG. 9, a seventh embodiment of the invention is seen. The seventh embodiment is similar in many respects to the fourth embodiment and is described in a manner where like parts are given like numbers incremented by '300'. Thus, a system 610 includes an aspiration catheter 620, a microcatheter 630, and a guidewire subassembly 640. The aspiration catheter and microcatheter may be identical to, or substantially the same as their counterparts in the system 310 of FIG. 6. The guidewire subassembly 640 of system 610, however, is different from subassembly 340 in that subassembly 640 includes a conical seal 666 that is constructed similarly to proximal seal 70d shown in FIG. 1e. Also, the guidewire subassembly 640 does not include the weeping or microjet balloon 370 of the fourth embodiment. In fact, the guidewire subassembly 640 particularly does not include any balloon. Thus, the guidewire subassembly can be said to consist of or to consist essentially of the guidewire core 650, the fluid transport element 662, and the conical seal 666, and optionally of a polymeric thin layer element 665 as described in more detail below. When "consisting essentially of" language is used herein with respect to the guidewire subassembly, such language is used to rule out the use of a balloon that will otherwise constitute a change in the material scope of the guidewire subassembly because it will add thickness to the subassembly, and during use to provide infusate to a blood vessel will require higher pressures. When "consisting of" language is used herein with respect to the guidewire subassembly, such language is intended to rule out the use of not only the balloon, but other elements that add function.

In one embodiment, the guidewire core 650 is constructed of a wire having a diameter of approximately 0.014 inches from its proximal end to a distal tapering diameter portion 650a. In one embodiment, the tapering diameter portion 650a is between approximately 1 to 3.3 inches in length, and the guidewire core tapers down to approximately 0.003 inches at or adjacent its distal tip 650b.

A coil or fluid transport element 662 extends over the tapering diameter portion 650a of the guidewire. The coil element 662 is constructed of helically wound platinum/stainless steel or Nitinol wire, which in one embodiment has a wire diameter of approximately 0.003 inches. In one embodiment, the coil element 660 includes (i) a tight pitch, closed wound first portion 662a having a length of approximately 0.2 to 0.7 inches, (ii) a loose pitch, open wound second portion 662b having a length of approximately 0.2 to 0.7 inches, (iii) a tight pitch, closed wound third portion 662c having a length of approximately 0.2 to 0.7 inches or more, (iv) a loose pitch, open wound fourth portion 662d having a length of approximately 0.2 to 0.7 inches, (v) a tight pitch, closed wound fifth portion 662e having a length of approximately 0.2 to 0.5 inches, and (vi) a loose pitch, open wound sixth portion 662f having a length of approximately 0.08 to 0.25 inches. The first portion 662a of the coil element is connected to the core wire 650 at or adjacent the proximal end of the tapering diameter portion 650a. The open wound second portion 662b of the coil element defines at least one inlet opening that permits infusate within the microcatheter 630 to flow between the coil element and the tapering diameter portion 650a of the guidewire core 650 (as indicated by arrows 664a). The closed wound third portion 662c is optionally coated with a polymeric thin layer 665, typically approximately 0.001 to 0.003 inches in material thickness, that fluid seals the third portion 662c yet maintains the flexibility of the coil element 662. The length of the layer 665 can be relatively longer or shorter than that shown in FIG. 9 with respect to the distal end of microcatheter 630. The conical seal 666 is interposed between an inner surface of microcatheter 630 and the outer surface of polymeric thin layer 665 forming a seal therebetween. In one embodiment, the polymeric thin layer 665 is integral with the conical seal and extends distally therefrom. The conical seal 666 is not directly attached to the microcatheter 630 and flares out to an outer diameter slightly larger than the inner diameter of the microcatheter 630 such that the seal 666 is always under compression by the inner surface of the microcatheter 630 and prevents infusate from exiting the distal end of the microcatheter as long as the seal 666 is within the microcatheter.

The open wound fourth portion 662d defines at least one outlet opening that permits infusate within the coil element to flow out of the coil element 662. The distal end of the core wire 650 and the distal end of the coil element 662 are provided with a blunt atraumatic tip 667 that may be integrally formed with the core wire 650. In one example, a polymer 668 is injected into the open wound sixth portion 662f of the coil element 662 to permanently fluid seal the distal tip 640a of the guidewire subassembly 640.

In one embodiment, a portion of the coil or fluid transport element that defines at least one outlet opening has multiple spaced outlet openings. The multiple spaced outlet openings may be evenly spaced or may be spaced in a non-even manner. In one embodiment, the multiple spaced openings are all of the same opening dimensions. In another embodiment, the multiple spaced openings have different opening dimensions. By way of example only, the openings can increase in dimension as they extend distally away from the microcatheter.

The guidewire/catheter system 610 may be used as follows. First, an blood vessel (not shown) is punctured and a sheath (not shown) inserted. A steerable guidewire (not shown) is inserted into the sheath and steered until it crosses the location (e.g., clot) of interest (not shown). The sheath may then be removed, and the aspiration catheter 620 is inserted through the puncture over the steerable guidewire and up to just proximal the clot. The microcatheter 630 is then fed between the aspiration catheter 620 and the guidewire until it extends out of the aspiration catheter and into or near the clot. The steerable guidewire is then removed, and the guidewire subassembly 640, comprising with the guidewire 650 and coil element 662, is inserted into the microcatheter 630 and snaked through the microcatheter until the open wound fourth portion 662d of the coil element is located in the clot (with the distal end 650c of the guidewire typically extending past the clot). Alternatively, the guidewire subassembly 640 may be used initially to function in place of the steerable guidewire, thereby eliminating the need for the steerable guidewire and reducing the number of insertion steps. Infusate (e.g., tPA) is then injected into the microcatheter 630, enters the open wound second portion 662b of the coil element 662, flows between the tapered diameter portion of the core wire 650a and the coil element 662, and out of open wound fourth portion 662d. As will be appreciated, only a small amount of pressure need be applied to the infusate to cause the infusate to disperse out the open wound fourth portion 662d and into the clot or into the walls of the blood vessel (not shown). When sufficient infusate has been introduced into the clot or vessel walls, the pressure is removed. The microcatheter 630 and guidewire subassembly 640 are then removed from the aspiration catheter 620. Suction may then be applied to the aspiration catheter 620 in order to remove the clot. The aspiration catheter 620 is then removed, the sheath (if present) is removed, and the blood vessel (not shown) is closed.

It will be appreciated that the system 610 of the seventh embodiment shown in FIG. 9 can be modified to include a weeping or microjet balloon, such as the balloon 370 of the fourth embodiment. For example, the proximal end 370a of the balloon 370 can be bonded over the polymeric thin layer 665 or directly to the windings of the closed wound third portion 662c, and the distal end 370c of the balloon can be bonded to the close wound fifth portion 662e. With the balloon 370 added to the system 610 described above, the open wound fourth portion 662d can permit infusate within the coil element to flow out of the coil element 662 and into the surrounding balloon 370 in similar manner as described above with respect to system 310 of the fourth embodiment. With the balloon, higher pressures are applied to the infusate in order to cause the infusate to inflate and weep out of the balloon 370.

Figure 10:
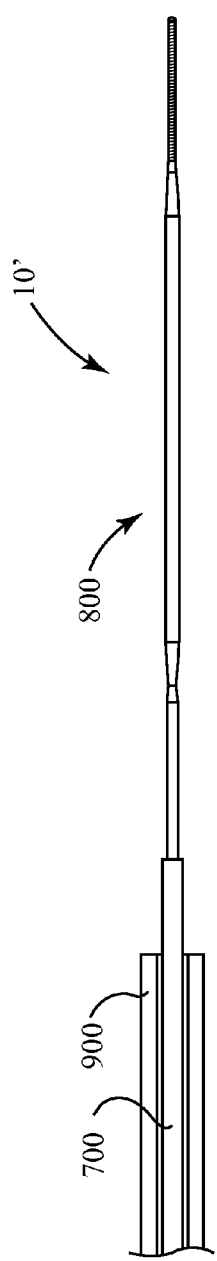
FIG. 10 is a fragmentary, enlarged, side elevational view of an eighth embodiment of a guidewire system within support and guiding catheters and with an optional balloon in a deflated condition.
Figure 11:
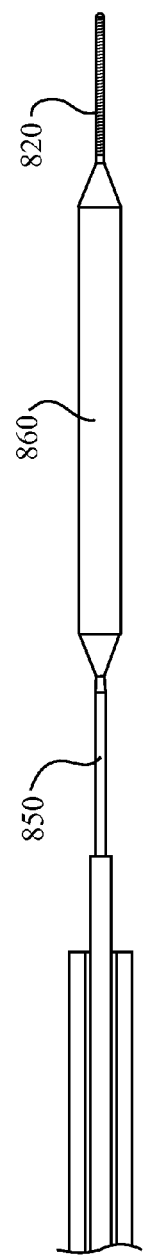
FIG. 11 is a fragmentary, enlarged, side elevational view of the system of FIG. 10 with the optional balloon in an inflated condition.
Figure 12:
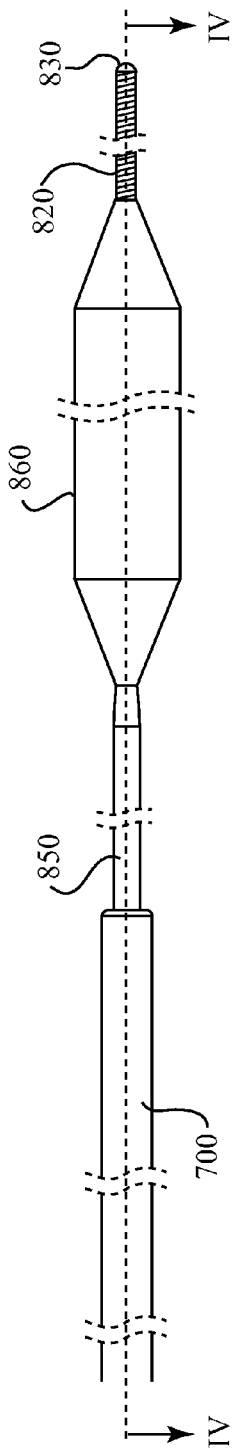
FIG. 12 is a fragmentary, further-enlarged, side elevational view of the system of FIG. 10 with the optional balloon in an inflated condition and without the guiding catheter.

FIGS. 10 to 12 illustrate aspects of an eighth embodiment of a catheter/guidewire system 10', which can be useful for treating atherosclerosis and blood clots in the peripheral vasculature of a patient. The catheter/guidewire system 10' includes a microcatheter sheath 700, a guidewire assembly 800, and a guiding catheter 900 or other support catheter. In the exemplary embodiment illustrated, the guiding catheter 900 is approximately 70 cm-100 cm in length if it is to be introduced through the femoral artery or approximately 30 cm-80 cm in length if it is to be introduced through the brachial artery, and has an inner diameter of between about 1.016 mm to 1.524 mm (0.040 inch and 0.060 inch) and an outer diameter of between about 1.524 mm to 2.54 mm (0.060 inch and 0.10 inch).

In the exemplary embodiment shown, the microcatheter sheath 700 is longer than the guiding catheter 900 by about 30 cm to 40 cm (11.8 inches to 15.7 inches) and is insertable slidably through the guiding catheter 900. The microcatheter sheath 100 has an inner diameter of between about 0.508 mm and 1.00 mm (0.020 inch and 0.040 inch) and an outer diameter of about 0.5842 mm to 0.8382 mm (0.023 inch to 0.033 inch), with a wall thickness of approximately 0.0762 mm (0.003 inch). In an exemplary embodiment, the microcatheter sheath 700 is formed from a plastic extrusion with a stainless steel coil or braid.

The guidewire subassembly 800 is slightly longer than the microcatheter sheath 100 by about 70 cm (27.6 inches) and is insertable slidably through the microcatheter sheath 700. In another exemplary embodiment where the distances to the treatment site are shorter, the guiding catheter 900 is approximately 30 cm long, the microcatheter sheath 700 is approximately 50 cm long, and the guidewire subassembly 800 is approximately 80 cm long.

The guidewire subassembly 800 includes a guidewire core 810 at its center (see FIGS. 13 and 14), a guidewire coil 820, a distal guidewire tip 830, a proximal seal sub-assembly 840, an optional transition tube or liner 850, and, optionally, a balloon 860. As seen best in FIG. 13, the guidewire core 810 runs from a proximal portion of the guidewire subassembly 800 all the way to the distal guidewire tip 830. The guidewire tip 830 can be integral with the guidewire core 810 or it can be secured thereto by a number of connection processes, including brazing and welding, for example. In an exemplary embodiment, the guidewire core 810 is of stainless steel, Nitinol, or from another very flexible material.

The guidewire coil 820 starts, in this exemplary embodiment, proximal of the seal subassembly 840. For secure attachment of the guidewire coil 820 to the guidewire core 810, the guidewire core 810 is formed with a reduction 812 adjacent the proximal end of the guidewire coil 820. The reduction 812 has an outer diameter that is approximately equal to or slightly greater than an inner diameter of the proximal end of the guidewire coil 820 for a secure fit that prevents the guidewire coil 820 from moving with respect to the guidewire core 810 after attachment thereto. The attachment can be any connection, such as welding or brazing. If, in an exemplary embodiment, the guidewire core 810 is of stainless steel, then the guidewire coil 820 can be of stainless steel, nitinol or a radiopaque metal such as platinum for easy connection thereto, for example, by soldering. It is equally possible to have the guidewire coil 820 extend proximally all the way to a proximal end of the guidewire core 810.

In an exemplary embodiment, the guidewire core 810 is constructed of a wire having a diameter of approximately 0.3556 mm (0.014 inch) from its proximal end to the intermediate tapered reduction 812. The reduction 812 is approximately 1 inch to 3.3 inches in length, and the guidewire core tapers down to approximately 0.762 mm (0.003 inch), which continues up to or adjacent the distal tip 830.

In the area of the reduction 812, the turns of the guidewire coil 820 are adjacent one another or are just slightly separated from one another. In such a configuration, where the guidewire coil 810 is attached, the individual coils are supported by the guidewire core 810 along the longitudinal extent thereof. Just distal of the reduction 812, where the guidewire core 810 is of a reduced diameter as compared to proximal of the reduction 812, the individual 821 coils separate from one another, as shown within the section circle of FIG. 13 and in the proximal side (left) of FIG. 14. This separation providing an entrance of a flow passage (or inlet opening) as will be explained in further detail below.

Both the guidewire core 810 and the guidewire coil 820 are shown as extending distally out of microcatheter sheath 700 and they do so in order to perform fluid transfer, such as to inflate the optional balloon 860. The inner diameter of the guidewire coil 820 surrounding the guidewire core 810 is larger than the outer diameter of the guidewire core 810 therewithin. This sizing creates a flow passage 822 through which inflation infusate or fluid can readily pass. As used herein, infusate and fluid are used interchangeably. In an exemplary embodiment, the spacing between the outer diameter of the guidewire core 810 and the inner diameter of the guidewire coil 820 is about 0.0254 mm to 0.0762 mm (0.001 inch to 0.003 inch), in particular, approximately 0.0508 mm (0.002 inch). The outer diameter of the guidewire coil 820 surrounding the guidewire core 810 is smaller than the inner diameter of the microcatheter sheath 700, as shown in the enlarged drawing of FIG. 14 (but, as expressed herein, this is not necessarily drawn to scale), so that the microcatheter sheath 700 can slide over the guidewire core 810 and guidewire coil 820. The outer diameter of the guidewire coil 820 is also, in an exemplary embodiment, the same outer diameter as the portion of the guidewire core 810 proximal of the guidewire coil 820.

To effect a fluid-tight (i.e., infusate-tight) seal for any fluid that is passing from the proximal end of the system 10' through the microcatheter sheath 700 distally (e.g., for being dispensed from one or more outlet openings of the coil 820—and optionally then through the balloon 860, if provided), the proximal seal sub-assembly 840 is provided and surrounds the guidewire coil 820. The proximal seal sub-assembly 840 has an outer diameter at least equal to or slightly greater than the inner diameter of the microcatheter sheath 700. In this way, the seal subassembly 840 provides the outermost edge of a fluid-tight seal at or near the distal interior 702 of the microcatheter sheath 700. In particular, with regard to FIG. 14, an outer proximal portion 842 of the proximal seal sub-assembly 840 contacts the inner surface of the microcatheter sheath 700 along its entire circumference. This contact forms an infusate-tight seal preventing fluid inside the proximal interior 704 of the microcatheter sheath 700 from exiting distally out the distal interior 702 of the microcatheter sheath 700. In an exemplary embodiment, the proximal seal sub-assembly 840 is made of urethane or polyurethane. In the exemplary embodiment of the system 10' in FIGS. 10 to 14, the proximal seal sub-assembly 840 does not thicken/project inward all the way to the outer surface of the guidewire coil 820. Instead, the outer proximal portion 842 of the proximal seal sub-assembly 840 tapers inwards to a distal portion 844 having an inner diameter sized to be at a given distance away from the outer circumferential surface of the guidewire coil 820. The distal portion 844 of the proximal seal sub-assembly 840 has an interior cylindrical bore 846 with a diameter sufficient to fit therewithin a proximal end of the hollow transition tube 850.

According to one aspect, the optional transition tube or liner 850 can serve to line the inside or outside of the guidewire coil 820 so as to prevent leakage of fluid from the coil 820. According to another aspect, the optional transition tube or liner 850 can serve to expedite the bonding of an optional balloon to the subassembly. According to another aspect, the optional transition tube or liner can serve to expedite the bonding of the seal 840 to the coil 820. In one aspect, where the guidewire coil 820 is sufficiently tightly wound between the inlet and outlet openings, and a balloon is not being utilized, it may not be necessary to utilize the transition tube or liner 850, as the bond between the seal 840 and coil 820 will not be subject to large pressures.

Figure 15:
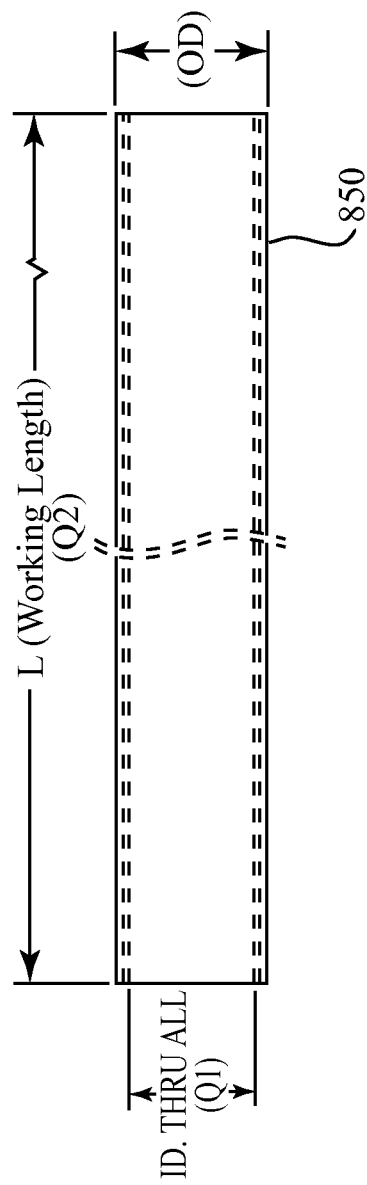
FIG. 15 is a fragmentary, enlarged, longitudinal, side elevational and partially hidden view of a coextruded transition tube of the system of FIG. 10.
Figure 16:
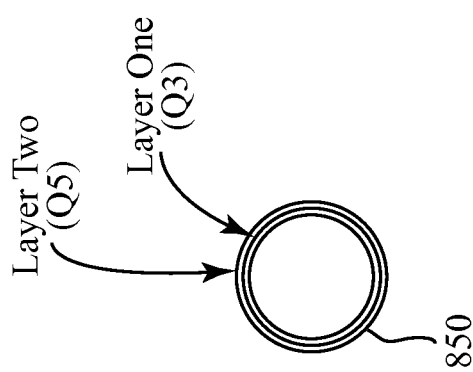
FIG. 16 is an elevational view of the tube of FIG. 15 from an end thereof.

In an exemplary embodiment, the optional hollow transition tube 850 may be a coextrusion of polyurethane on an outer surface of a nylon interior. This coextrusion is depicted, for example, in FIGS. 15 and 16. In this way, the outer surface of the proximal end of the transition tube 850 can be fluid-tightly connected to the inner surface of the cylindrical bore 846 of the proximal seal sub-assembly 840 easily because urethanes easily bond or heat seal to one another. Such connection also completes the fluid-tight seal preventing any fluid travelling distally from the proximal end of the microcatheter sheath 700 from exiting out the distal interior 702 of the microcatheter sheath. One exemplary embodiment of the transition tube 850 has an overall length of about 9 cm to 11 cm (3.54 inches to 4.33 inches), in particular, of about 10 cm (3.94 inches). The thickness of the outer polyurethane layer is about 0.0127 mm to 0.0508 mm (0.0005 inch to 0.002 inch), in particular, about 0.0254 mm (0.001 inch). The outer diameter of the polyurethane layer is about 0.4064 mm to 0.508 mm (0.016 inch to 0.020 inch), in particular, about 0.4572 mm (0.018 inch). The thickness of the inner nylon layer is about 0.0127 mm to 0.0508 mm (0.0005 inch to 0.002 inch), in particular, about 0.0254 mm (0.001 inch). The inner diameter of the nylon layer is about 0.3048 mm to 0.4064 mm (0.012 inch to 0.016 inch), in particular, about 0.3556 mm (0.014 inch).

With such an exemplary configuration, the interior bore of the transition tube 850 is adjacent or just touching the outer surface of the guidewire coil 820. If there is a gap between the interior bore of the transition tube 850 and the outer surface of the guidewire coil 820, then fluid could pass through the gap distally. Fluid can fill such a gap, but if it does, this does not present a problem of leakage in embodiments where the optional balloon 860 is present because the gap ends distally within the interior of the balloon 860. If there is little or no gap between the interior bore of the transition tube 850 and the outer surface of the guidewire coil 820, then fluid passes substantially or only through the flow passage 822.

The optional balloon 860 is provided with a proximal leg 862 shaped to fit inside the hollow distal end of the transition tube 850. In one exemplary embodiment, the balloon 860 is made of nylon. As such, the inner surface of the distal end of the transition tube 850 can be fluid-tightly sealed to the outer surface of the proximal leg 862 of the balloon easily because nylon readily bonds to itself, for example, by heat-fusing. Alternatively, the attachment can be to the inner surface of the proximal leg 862.

The materials comprising the outer proximal portion 842 of the seal assembly 840 may include, for example, urethane, polyurethane, polyisoprene, and kraton. This means that the outer proximal portion 842 is compliant—it can stretch at least a little. As such, when exposed to the high pressures within the catheter 10', at least a portion distal of the very proximal-most end of the outer proximal portion 842 expands outwards from the inwardly conical taper to provide an even stronger seal against the microcatheter sheath 700 to thereby further inhibit leakage of the balloon inflation fluid that is being exposed to the high pressures discussed herein.

Continuing from the proximal leg 862 distally, the optional balloon 860 tapers outwardly in a proximal transition zone 864 about the guidewire coil 820 and the guidewire core 810. In the exemplary embodiment illustrated, a compression zone or treatment portion 866 of the optional balloon 860 extends with a constant diameter from the proximal transition zone 864 to a distal transition zone 868, which tapers inwardly to a distal leg 869. The taper of both the transition zones 864, 868 can be symmetrical or asymmetrical, straight, polygonal, and/or curved. The compression zone 866 of the balloon 860 is the area at which the balloon 860 touches the interior vessel walls during clinical treatment.

Spaced from and distal the inlet opening of the coil, and at an intermediate portion of the balloon 860, if provided, the individual coils 821 of guidewire coil 820 are again separated from one another as shown in FIG. 13 to provide an outlet opening. The separation of the coils at the inlet and outlet openings is in contrast to other areas of the guidewire coil 820 where the individual coils are closely adjacent one another or touching one another. With such a configuration, any fluid that enters the flow passage 822 through the inlet opening will exit the flow passage 822 between these separated coil(s) 821 (i.e., at the outlet opening), and directly into the interior 867 of the balloon 860, when provided. However, if the balloon 860 is omitted, the fluid will simply exit the flow passage 822 between the separated coils 821.

If the balloon 860 is provided, in order to prevent any fluid from exiting the balloon 860 at the distal leg 869, the distal leg 869 is sealed to the guidewire coil 820 and/or the guidewire core 810. In an exemplary embodiment of the distal end of the system 10', a distal section of the guidewire coil 820 is fastened to a corresponding distal section of the guidewire core 810. In one exemplary embodiment, the fastened section of the guidewire coil 820 and guidewire core 810 extends from just proximal of the proximal end of the distal leg 869 of the optional balloon 860 to just distal of the distal end of the distal leg 869 of the balloon 860. The longitudinal size of this fastened section need not be this particular length. Any length is sufficient as long as fluid cannot exit the interior 867 of the balloon 860 through the distal leg 869 when the distal leg 869 is fastened to the interior guidewire coil 820/guidewire core 810. The length is also sufficient to be used for breaching a clot or other obstruction. One exemplary process for sealing and fastening the guidewire coil 820 to the guidewire core 810 is brazing. After the brazed connection is performed, the distal leg 869 (e.g., of nylon) can be heat-fused to the brazed distal end to thereby create a fluid-tight seal at the distal leg 869 and prevent fluid from exiting out from the distal leg 869 of the balloon 860. Alternatively, a non-illustrated sleeve having an interior surface sealable to the guidewire coil 820 and an exterior surface sealable to the interior surface of the distal leg 869 is equally possible. A further alternative has the sleeve sandwich the distal leg 869 to the guidewire coil 820. The optional balloon 860 is seen in a fully deflated (unexpanded) state in FIG. 10 and in at least a partially inflated state in FIGS. 11, 12, and 13.

The design of the guidewire subassembly 800 allows construction of the entire catheter system 10' with elements having very small outer diameters. In particular, the total outer diameter of the microcathether sheath 700, including the balloon-guidewire subassembly 800 therein, is less than approximately 3 mm. This size permits the system 10' to be effectively used in smaller vessels than permitted with other known devices, in particular, in vessels having less than a 3 mm inner diameter.

Because the size of the vessel in which the optional balloon 860 is to be inflated is so small, it is desirable to have the optional balloon inflated 860 with high pressure to treat the atherosclerosis or blood clot. High-pressure or high-pressures, as referred to herein, start at about 5 atmospheres (73.5 psi) and go up to between 8 atmospheres and 12 atmospheres (117.6 psi to 176 psi), in particular, they are at approximately 10 atmospheres (147 psi). The optional balloon 860 of the embodiments describe herein is substantially non-compliant or semi-compliant. This means that, even with the high pressures in which it is inflated, the optional balloon 860 will not stray from its pre-defined and intended shape. The optional balloon 860, therefore, may be made from Nylon or high durometer polyurethane or other materials suitable for use in a high pressure non-compliant or semicompliant balloons. The optional balloon 860 is between about 0.0254 mm and 0.2032 mm (0.0004 inch and 0.002 inch) thick, between about 10 mm and 50 mm (0.4 inch and 0.8 inch) long and is capable of having a nominal expanded diameter of no more than about 4 mm (0.18 inch).

In one exemplary non-illustrated embodiment, a cage element or balloon-expandable stent is provided around the balloon 860. The proximal end of the cage element may be attached fixedly or removably to the balloon 860, in this sense, the cage acts as a support in the former case and a removable stent in the latter. For example, the proximal end of the cage element may be attached fixedly or removably to the distal end of the balloon 860 or to the distal end of the microcatheter sheath 700. In another exemplary embodiment, the proximal end of the cage element is attached to either the distal end of the transition tube 850 or to the distal end of the guidewire coil 820 or may be attached to the balloon 860 where the balloon attaches to the transition tube 850 or to the guidewire coil 820. In another exemplary embodiment where a stent is to be provided, the stent is merely crimped on the balloon 860. When installed, the stent remains open after the balloon 860 inflates and deflates to keep the clot open and allow blood to flow to the vessels that were affected by the clot.

A ninth embodiment is shown in FIG. 17. This embodiment is similar in many respects to the embodiment of FIGS. 10 to 16 and is described in a manner where like parts are given like numbers (increased by "1000"). Thus, system 1010' includes a microcatheter sheath 1700 (in dashed lines), a guidewire subassembly 1800, and a guiding catheter 1900 (in dashed lines). The guidewire subassembly 1800 includes a guidewire core 1810, a guidewire coil 1820, a distal tip (not shown), a seal subassembly 1840, an optional transition tube or liner 1850, and an optional balloon 1860. All of these elements may be identical to, or substantially the same as their counterparts in the system 10' of FIGS. 10 to 16. The system 1010', however, utilizes a different seal and a different optional transition tube. Where other features in the system 1010' are similar to the previous system 10', they are not repeated.

In the exemplary embodiment illustrated, the guiding catheter 1900 is approximately 70 cm-100 cm in length if it is to be introduced through the femoral artery or approximately 30 cm-80 cm in length if it is to be introduced through the brachial artery, and has an inner diameter of between about 1.016 mm to 1.524 mm (0.040 inch and 0.060 inch) and an outer diameter of between about 1.524 mm to 2.54 mm (0.060 inch and 0.10 inch).

In the exemplary embodiment shown, the microcatheter sheath 1700 is longer than the guiding catheter 1900 by about 30 cm to 40 cm (11.8 inches to 15.7 inches) and is insertable slidably through the guiding catheter 1900. The microcatheter sheath 1700 has an inner diameter of between about 0.508 mm and 0.762 mm (0.020 inch and 0.030 inch) and an outer diameter of approximately 0.5842 mm to 0.8382 mm (0.023 inch to 0.033 inch), with a wall thickness of approximately 0.0762 mm (0.003 inch). In an exemplary embodiment, the microcatheter sheath 1700 is formed from a plastic extrusion with a stainless steel coil or braid.

The guidewire subassembly 1800 is slightly longer than the microcatheter sheath 1700 by about 70 cm (27.6 inches) and is insertable slidably through the microcatheter sheath 1700. In another exemplary embodiment where the distances to the treatment site are shorter, the guiding catheter 900 is approximately 30 cm long, the microcatheter sheath 700 is approximately 50 cm long, and the guidewire subassembly 800 is approximately 80 cm long.

Both the guidewire core 1810 and the guidewire coil 1820 are shown in FIG. 8 extended distally out of the microcatheter sheath 1700. The inner diameter of the guidewire coil 1820 surrounding the guidewire core 1810 is larger than the outer diameter of the guidewire core 1810 therewithin (except at the proximal inwardly reducing transition zone of the guidewire core 1810 where the proximal end of the guidewire coil 1820 is attached). As in previous embodiments, the one or more coils 1821 distal of the guidewire core-to-guidewire coil attachment area are separated from one another. This configuration creates a flow passage 1822 through which fluid can easily pass. In an exemplary embodiment, the spacing between the outer diameter of the guidewire core 1810 and the inner diameter of the guidewire coil 1820 distal of the connection area is about 0.0254 mm to 0.0762 mm (0.001 inch to 0.003 inch), in particular, approximately 0.0508 mm (0.002 inch). The outer diameter of the guidewire coil 1820 surrounding the guidewire core 1810 is smaller than the inner diameter of the microcatheter sheath 1700, as shown in the enlarged drawing of FIG. 17 (which is not to scale).

To effect a fluid-tight seal for any fluid that is passing from the proximal end of the system 1010' through the microcatheter sheath 1700 distally, the proximal seal sub-assembly 1840 surrounds the guidewire coil 1820. The proximal seal subassembly 1840 has an outer diameter at least equal to or slightly greater than the inner diameter of the microcatheter sheath 1700. In this way, the seal sub-assembly 1840 provides the outermost edge of a fluid-tight seal at the distal interior 1702 of the microcatheter sheath 1700. In particular, an outer proximal portion of the proximal seal sub-assembly 1840 contacts the inner surface of the microcatheter sheath 1700 along its entire circumference. The proximal portion of the seal sub-assembly 1840 in this exemplary embodiment projects inwards all the way to touch the outer surface of the guidewire coil 1820 in a fluid-tight fit that does not leak with the high pressures experienced with this system. In an exemplary embodiment, the proximal seal sub-assembly 1840 is made of urethane or polyurethane. This means that the outer proximal portion 1842 is compliant. As such, when exposed to the high pressures within the catheter 1010', at least a portion distal of the very proximal-most edge of the outer proximal portion 1842 expands outwards from the inwardly conical taper to provide an even stronger seal against the microcatheter sheath 1700 to thereby inhibit leakage of the balloon inflation fluid that is being exposed to the high pressures discussed herein.

The inner and outer radial contact (with the microcatheter sheath 1700 and the guidewire coil 1820, respectively) forms a fluid-tight seal preventing fluid inside the interior 1704 of the microcatheter sheath 1700 from exiting distally out the distal interior 1702 of the microcatheter sheath 1700.

The proximal leg 1862 of the balloon 1860 has an inner diameter sized to fit the outer circumferential surface of the guidewire coil 1820 tightly. The proximal leg 1862 is fluid-tightly connected to the outer circumferential surface of the guidewire coil 1820, for example, by UV bonding.

In this exemplary embodiment, the optional hollow transition liner 1850 is sized to tightly fit inside the guidewire coil 1820 and extend at least to both the distal portion of the seal subassembly 1840 and to the proximal leg 1862 of the balloon 1860. In particular, the exemplary embodiment shown in FIG. 17 extends from almost the proximal edge of the distal portion of the seal sub-assembly 1840 all the way through the proximal leg 1862 of the optional balloon 1860 and up to the first coil 1824 of the guidewire coil 1820 that is separated from the adjacent coil for transmitting fluid therethrough. In such a configuration, therefore, the guidewire coil 1820 is sandwiched between the transition liner 1850 on the inside side and the seal-subassembly 1840 and the proximal leg 1862 on the opposing outer side. In particular, the outer surface of the proximal end of the transition tube 1850 is fluid-tightly connected to the inner surface of the guidewire coil 1820. The inner surfaces of the distal portion of the seal sub-assembly 1840 and the proximal leg 1862 of the optional balloon 1860 are both fluid-tightly connected to the exterior surface of the guidewire coil 1820 to thereby create a fluid-tight passageway within the guidewire coil 1820 and around the guidewire core 1810.

Such a connection completes the fluid-tight seal to prevent any fluid, travelling distally from the proximal end of the microcatheter sheath 1700, from exiting out the microcatheter sheath 1700. One exemplary embodiment of the optional transition liner 1850 has an overall length of about 2 cm to 11 cm (3.54 inches to 4.33 inches), in particular, about 5 cm (3.94 inches). The thickness of the optional transition tube 1250 is about 0.0127 mm to 0.0508 mm (0.0005 inch to 0.002 inch), in particular, about 0.0254 mm (0.001 inch). The outer diameter of the optional transition tube 1250 is about 0.4064 mm to 0.508 mm (0.016 inch to 0.020 inch), in particular, about 0.4572 mm (0.018 inch).

With such an exemplary configuration, the fluid originating from the proximal end of the microcatheter sheath 1700, for example, passes entirely through the flow passage 1822 and into the interior 1867 of the optional balloon 1860. The transition liner 1850 can be made of a material that is non-compliant, i.e., it does not expand under pressure from balloon inflation fluid under high pressure. Alternatively and/or additionally, the guidewire coil 1820 can be sufficiently strong in its radial dimension to prevent the transition liner 1850 from expanding radially and/or inflating under pressure during inflation of the balloon 1860 at the high balloon-inflation pressures.

In an exemplary embodiment, the optional balloon 1860 is made of nylon. Continuing from the proximal leg 1862 distally, the balloon 1860 tapers outwardly about the guidewire coil 1820 (and the guidewire core 1810) in a proximal transition zone 1864. In the exemplary embodiment illustrated, a compression zone or treatment portion 1866 of the optional balloon 1860 extends with a constant diameter from the proximal transition zone 1864 to a distal transition zone 1868, which tapers inwardly to a distal leg 1869. The compression zone 1866 of the optional balloon 1860 is the area at which the balloon 1860 touches the interior vessel walls during clinical treatment, which is explained in further detail below. The tapers of the proximal and distal transition zones 1864, 1868 can be symmetrical or asymmetrical, straight, curved, or polygonal.

As in the portion of the guidewire coil 1820 proximal of the outer proximal portion 1842 where some coils 1821 are slightly separated from one another to create an entrance (inlet) of a flow passage 1822, at least in an intermediate portion of the balloon 1860 distal of the distal end of the optional transition liner 1850, other individual coils 1821 of the guidewire coil 1820 are separated from one another as shown in FIG. 17 to create an outlet. The separation of the individual coils at the inlet and outlet is in contrast to other areas of the guidewire coil 1820 where the individual coils are closely adjacent one another or touching one another. With such a configuration, any fluid that enters the flow passage 1822 at the inlet will exit the flow passage 1822 between these separated distal coil(s) 1821 at the outlet, and will flow into the interior 1867 of the balloon 1860 when present. However, where the optional balloon 1860 is not present, the fluid will simply exit from the spaces between separated distal coil(s) 1821 into the vessel surrounding those spaces.

The design of the guidewire subassembly 1800 allows construction of the entire catheter system 1010' with elements having very small outer diameters. In particular, the total outer diameter of the microcathether sheath 1700, including the guidewire subassembly 1800 therein, is less than approximately 3 mm. This size permits the system 1010' to be effectively used in smaller vessels than permitted with other known devices, in particular, in vessels having less than a 3 mm inner diameter.

A tenth exemplary embodiment is shown in FIG. 18. This embodiment is similar in many respects to the embodiments of FIGS. 10 to 16 and 17 and is described in a manner where like parts are given like numbers that are two-thousand or one-thousand apart, respectively. Thus, system 2010' includes a microcatheter sheath 2700 (in dashed lines), a guidewire subassembly 2800, and a guiding catheter 2900 (in dashed lines). The guidewire subassembly 2800 includes a guidewire core 2810, a guidewire coil 2820, a distal tip 2830, a seal subassembly 2840, an optional transition tube or liner 2850, and a an optional balloon 2860. All of these elements may be identical to, or substantially the same as their counterparts in the systems 10', 1010' of FIGS. 10 to 16. The system 2010', however, utilizes a different seal and a different optional transition tube. Where other features in the system 2010' are similar to the previous systems 10', 1010', they are not repeated.

In the exemplary embodiment illustrated, the guiding catheter 2900 is approximately 70 cm-100 cm in length if it is to be introduced through the femoral artery or approximately 30 cm-80 cm in length if it is to be introduced through the brachial artery, and has an inner diameter of between about 1.016 mm to 1.524 mm (0.040 inch and 0.060 inch) and an outer diameter of between about 1.524 to 2.54 mm (0.060 inch and 0.10 inch).

In the exemplary embodiment shown, the microcatheter sheath 2700 is longer than the guiding catheter 2900 by about 30 cm to 40 cm (11.8 inches to 15.7 inches) and is insertable slidably through the guiding catheter 2900. The microcatheter sheath 2700 has an inner diameter of between about 0.508 mm and 0.762 mm (0.020 inch and 0.030 inch) and an outer diameter of approximately 0.5842 mm to 0.8382 mm (0.023 inch to 0.033 inch), with a wall thickness of approximately 0.0762 mm (0.003 inch). In an exemplary embodiment, the microcatheter sheath 2700 is formed from a plastic extrusion with a stainless steel coil or braid.

The guidewire subassembly 2800 is slightly longer than the microcatheter sheath 2700 by about 70 cm (27.6 inches) and is insertable slidably through the microcatheter sheath 2700. In another exemplary embodiment where the distances to the treatment site are shorter, the guiding catheter 2900 is approximately 30 cm long, the microcatheter sheath 2700 is approximately 50 cm long, and the guidewire subassembly 2800 is approximately 80 cm long.

The inner diameter of the guidewire coil 2820 surrounding the guidewire core 2810 is larger than the outer diameter of the guidewire core 2810 therewithin. This sizing creates a flow passage 2822 through which fluid can easily pass. In an exemplary embodiment, the spacing between the outer diameter of the guidewire core 2810 and the inner diameter of the guidewire coil 2820 is about 0.0254 mm to 0.0762 mm (0.001 inch to 0.003 inch), in particular, approximately 0.0508 mm (0.002 inch). The outer diameter of the guidewire coil 2820 surrounding the guidewire core 2810 is smaller than the inner diameter of the microcatheter sheath 2700, as shown in the enlarged drawing of FIG. 18.

To effect a fluid-tight seal for any fluid that is passing from the proximal end of the system 2010' through the microcatheter sheath 2700, the proximal seal sub-assembly 2840 surrounds the guidewire coil 2820. The proximal seal sub-assembly 2840 has an outer diameter at least equal to or slightly greater than the inner diameter of the microcatheter sheath 2700. In this way, the seal sub-assembly 2840 provides the outermost edge of a fluid-tight seal at the distal interior of the microcatheter sheath 2700. In particular, an outer proximal portion of the proximal seal sub-assembly 2840 contacts the inner surface of the microcatheter sheath 2700 along its entire circumference. The proximal portion of the seal sub-assembly 2840 in this exemplary embodiment projects inwards all the way to touch the outer surface of the guidewire coil 2820 in a fluid-tight fit that does not leak with the high pressures experienced with this system. In an exemplary embodiment, the proximal seal subassembly 2840 is made of urethane or polyurethane. This means that the outer proximal portion 2842 is compliant such that it can stretch at least a little. As such, when exposed to the high pressures within the catheter 2010', at least a portion distal of the very proximal-most edge of the outer proximal portion 2842 expands outwards from the inwardly conical taper to provide an even stronger seal against the microcatheter sheath 2700 to thereby inhibit leakage of the fluid that is being exposed to the high pressures discussed herein.

The proximal leg 2862 of the balloon 2860 has an inner diameter sized to fit the outer circumferential surface of the guidewire coil 2820 tightly. The proximal leg 2862 is fluid-tightly connected to the outer circumferential surface of the guidewire coil 2820, for example, by cyanoacrylate.

In this exemplary embodiment, the optional hollow transition tube 2850 is sized to tightly fit outside or inside the proximal leg 2862 of the optional balloon 2860, which is fused to the distal end of the transition tube 2850. The proximal end of the optional transition tube 2850 is fused to the outer proximal portion 2842 at the distal end 2844 thereof, either on the outside surface of the outer proximal portion 2842 or the inside surface. Each of these fused connections create a liquid tight seal that does not leak under high pressure. The inner surfaces of the distal portion of the seal sub-assembly 2840 and the proximal leg 2862 of the optional balloon 2860 are both fluid-tightly connected to the exterior surface of the guidewire coil 2820 to thereby create a fluid-tight passageway within the guidewire coil 2820 and around the guidewire core 2810.

Such a connection completes the fluid-tight seal to prevent any fluid, travelling distally from the proximal end of the microcatheter sheath 2700, from exiting out the microcatheter sheath 2700. One exemplary embodiment of the transition liner 2850 has an overall length of about 9 cm to 11 cm (3.54 inches to 4.33 inches), in particular, of about 10 cm (3.94 inches). The thickness of the transition tube 2850 is about 0.0127 mm to 0.0508 mm (0.0005 inch to 0.002 inch), in particular, about 0.0254 mm (0.001 inch). The outer diameter of the transition tube 2850 is about 0.4064 mm to 0.508 mm (0.016 inch to 0.020 inch), in particular, about 0.4572 mm (0.018 inches).

In an exemplary embodiment, the optional non-compliant balloon 2860 is made of nylon. The optional balloon 2860 may also be made from a semi-compliant material such as high durometer polyurethane. As before, like the portion of the guidewire coil 2820 proximal of the outer proximal portion 2842 where some coils 2821 are slightly separated from one another to create an entrance (inlet) of a flow path 2822, in at least in an intermediate portion of the optional balloon 2860 distal of the distal end of the transition liner 2850, individual non-illustrated coils of the guidewire coil 2820 are also separated from one another to create a flow path outlet. The separation of the coils at the inlet and outlet is in contrast to other areas of the guidewire coil 2820 where the individual coils are closely adjacent one another or touching one another. With such a configuration, any fluid that enters the flow passage 2822 inside the guidewire coil 2820 proximal of the transition liner 2850 will exit the flow passage between these separated coil(s), directly into the interior of the balloon 2860 when present. However, where optional balloon 2860 is not present, the fluid will simply exit the flow passage between the separated coils into the vessel surrounding the separated coil(s).

The optional transition liner 2850 can be made of a material that is non-compliant, i.e., it does not expand under pressure from balloon-inflation fluid under high pressure. Alternatively and/or additionally, the guidewire coil 2820 can be sufficiently strong in its radial dimension to prevent the optional transition liner 2850 from expanding radially and/or inflating under pressure during inflation of the balloon 2860 at the high balloon-inflation pressures. The optional transition liner 2850 is attached to the guidewire coil 2820 using cyanoacrylate, for example.

The design of the guidewire subassembly 2800 allows construction of the entire catheter system 2010' with elements having very small outer diameters. In particular, the total outer diameter of the microcathether sheath 2700, including the guidewire subassembly 2800 therein, is less than approximately 3 mm. This size permits the system 2010' to be effectively used in smaller vessels than permitted with other known devices, in particular, in vessels having less than a 3 mm inner diameter.

There have been described and illustrated herein several embodiments of a system and a method of treating the vasculature of a patient. While particular embodiments have been described, it is not intended that the invention be limited thereto, as it is intended that the invention be as broad in scope as the art will allow and that the specification be read likewise. While particular preferred diameters and sizes of catheters, elongate members, coils, balloons, and other elements have been disclosed, it will be appreciated that minor modifications to the shapes and sizes of the catheters, elongate members, coils, balloons and other members which also accomplish the functionality of the system may be utilized. Also, while particular procedures have been disclosed such as treating blood clots in arteries of a patient, it will be appreciated that the embodiments may be used to treat blood vessels regardless of whether or not the blood vessels contain clots. It will therefore be appreciated by those skilled in the art that yet other modifications could be made to the provided invention without deviating from its spirit and scope as claimed.

What is claimed is:

1. A system for use in a blood vessel in conjunction with an infusate, the system comprising:
   a microcatheter having an inner surface and a distal end, and said microcatheter providing a lumen through which the infusate can flow; and
   a guidewire subassembly extending through and beyond said distal end of said microcatheter, and longitudinally displaceable relative to said microcatheter, said guidewire subassembly consisting essentially of:
   (i) a guidewire core,
   (ii) a fluid transport element coupled to and extending around said guidewire core, said fluid transport element having a length along said guidewire core, said fluid transport element defining at least one inlet opening and at least one outlet opening spaced from said at least one inlet opening along a portion of the length of the fluid transport element, a fluid flow path being defined between said guidewire core and said fluid transport element, and
   (iii) a conical seal interposed between said fluid transport element and said microcatheter, for sealing therebetween and ensuring that infusate within said microcatheter is directed into said blood vessel only through said at least one outlet opening, wherein infusate can flow through said lumen of said microcatheter into said at least one inlet opening, along said fluid flow path, and out of said at least one outlet opening.

2. The system according to claim 1, further comprising:
   an aspiration catheter attachable to a source of suction, said microcatheter extending through said aspiration catheter.

3. The system according to claim 1, wherein:
   said guidewire core has a first diameter at a first location where said fluid transport element is attached to said guidewire core and a second diameter smaller than said first diameter at a second location distal said first location where said fluid transport element extends around said guidewire core.

4. The system according to claim 1, wherein:
   said fluid transport element includes a proximal portion attached to said guidewire core and including a distal support portion attached to said guidewire and an intermediate portion between the proximal portion and the distal support portion of said fluid transport element that is not attached to said guidewire.

5. The system according to claim 1, wherein:
   said fluid transport element is a coil element.

6. The system according to claim 5, wherein:
   said guidewire core has at least one tapered portion extending from a proximal end to a distal end and said coil element extends from said proximal end to said distal end of said tapered portion of said guidewire core.

7. The system according to claim 6, wherein:
   said coil element extends over said tapered portion of said guidewire core such that at least a portion of the path for infusate flow is provided between said tapered portion of said guidewire core and said coil element.

8. The system according to claim 5, wherein:
   said coil element is helical and wherein said at least one inlet opening is helical and said at least one outlet opening is helical.

9. The system according to claim 5, wherein:
   said coil element has
   (i) a tight pitch, closed wound first portion coupled to said guidewire core,
   (ii) a loose pitch, open wound second portion extending from said first portion and a proximal end of said conical seal and defining said at least one inlet opening through which the infusate can flow from said microcatheter to a flow path between said coil element and said guidewire core,
   (iii) a tight pitch, closed wound third portion extending from said second portion and to which a distal end of said conical seal is coupled,
   (iv) a loose pitch, open wound fourth portion extending from said third portion and defining said at least one outlet opening through which the infusate can flow out, and
   (v) a tight pitch, closed wound fifth portion extending from said fourth portion to a distal end of said guidewire core to which the fifth portion is coupled.

10. The system according to claim 9, wherein:
    said coil element further includes a polymer disposed within said fifth portion to seal said distal end of said guidewire subassembly to said fifth portion.

11. The system according to claim 1, wherein:
    said conical seal includes an integral distal polymeric thin layer portion attached to said fluid transport element.

12. The system according to claim 11, wherein:
    said conical seal extends proximally from said polymeric thin layer.

13. The system according to claim 1, wherein:
    said conical seal is tapered radially inwardly in a distal direction from a proximal end of the seal to a distal end of the seal.

14. A method for treating a blood clot in the vasculature of a patient, comprising:
    incising the patient to form an incision;
    distally advancing a system through the incision to a blood clot, the system consisting essentially of:
      a microcatheter having an inner surface and a distal end, and said microcatheter providing a lumen through which infusate can flow; and
      a guidewire subassembly extending through and beyond said distal end of said microcatheter, said guidewire subassembly consisting essentially of:
      (i) a guidewire core having at least one tapered portion extending from a proximal end of the at least one tapered portion to a distal end of the at least one tapered portion,
      (ii) a fluid transport element coupled to and extending around said tapered portion of said guidewire core, said fluid transport element defining at least one inlet opening and at least one outlet opening along a portion of a length of the fluid transport element, a fluid flow path being defined between said guidewire core and said fluid transport element,
      (iii) a conical seal interposed between said fluid transport element and said microcatheter for sealing therebetween, wherein infusate can flow through said lumen of said microcatheter into said at least one inlet opening, along said fluid flow path, and out through said at least one outlet opening,
    wherein said advancing comprises locating said at least one outlet opening adjacent or within the blood clot; and
    infusing a blood clot dissolving infusate into said lumen of said microcatheter, through said fluid flow path, and out of said at least one outlet opening to thereby contact the infusate with the blood clot.

15. A method according to claim 14, wherein:
said conical seal includes an integral distal polymeric thin layer portion attached to said fluid transport element.

\* \* \* \* \*